US010525025B2

(12) United States Patent
Ray, II

(10) Patent No.: US 10,525,025 B2
(45) Date of Patent: Jan. 7, 2020

(54) COMPOUNDED COMPOSITIONS AND METHODS FOR TREATING PAIN

(71) Applicant: CMPD Licensing, LLC, Conroe, TX (US)

(72) Inventor: Jay Richard Ray, II, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 0 days.

(21) Appl. No.: 16/381,967

(22) Filed: Apr. 11, 2019

(65) Prior Publication Data

US 2019/0231723 A1    Aug. 1, 2019

Related U.S. Application Data

(60) Continuation-in-part of application No. 16/010,731, filed on Jun. 18, 2018, which is a division of application No. 15/354,630, filed on Nov. 17, 2016, now Pat. No. 9,999,604.

(51) Int. Cl.
| | |
|---|---|
| *A61K 31/196* | (2006.01) |
| *A61K 31/167* | (2006.01) |
| *A61K 9/06* | (2006.01) |
| *A61K 47/10* | (2017.01) |
| *A61K 47/20* | (2006.01) |
| *A61P 23/02* | (2006.01) |
| *A61K 9/00* | (2006.01) |

(52) U.S. Cl.
CPC .......... *A61K 31/196* (2013.01); *A61K 9/0014* (2013.01); *A61K 9/06* (2013.01); *A61K 31/167* (2013.01); *A61K 47/10* (2013.01); *A61K 47/20* (2013.01); *A61P 23/02* (2018.01)

(58) Field of Classification Search
CPC ...... A61K 31/196; A61K 31/167; A61K 9/06; A61K 9/0014; A61K 47/10; A61K 47/20; A61P 23/02
See application file for complete search history.

(56) References Cited

U.S. PATENT DOCUMENTS

| | | |
|---|---|---|
| 4,711,906 A | 12/1987 | von Stetten |
| 5,407,663 A | 4/1995 | Eisen |
| 5,524,622 A | 6/1996 | Wilson |
| 5,603,943 A | 2/1997 | Yanagawa |
| 5,668,119 A | 9/1997 | Medencia |
| 6,066,629 A | 5/2000 | Moir et al. |
| 6,093,417 A | 7/2000 | Petrus |
| 6,299,608 B1 | 10/2001 | Solomon et al. |
| 8,084,445 B2 | 12/2011 | Huq et al. |
| 8,129,364 B2 | 3/2012 | Chaudry |
| 8,318,817 B2 | 11/2012 | Lichter et al. |
| 8,338,648 B2 | 12/2012 | Stock et al. |
| 8,663,663 B1 | 3/2014 | Ray |
| 9,078,853 B2 | 7/2015 | Ray |
| 9,999,604 B2 * | 6/2018 | Ray, II ................ A61K 31/196 |
| 2002/0061281 A1 | 5/2002 | Osbakken |
| 2003/0143162 A1 | 7/2003 | Speirs et al. |
| 2004/0235807 A1 | 11/2004 | Weinrich et al. |
| 2005/0004002 A1 | 1/2005 | Desai et al. |
| 2005/0053563 A1 | 3/2005 | Manissier et al. |
| 2005/0148570 A1 | 7/2005 | Huang et al. |
| 2006/0157507 A1 | 7/2006 | Chang et al. |
| 2006/0228306 A1 | 10/2006 | Lane |
| 2007/0037776 A1 | 2/2007 | Richardson et al. |
| 2007/0065373 A1 | 3/2007 | Morton et al. |
| 2007/0231274 A1 | 10/2007 | Bhasin |
| 2007/0293460 A1 | 12/2007 | Ray et al. |
| 2009/0048347 A1 * | 2/2009 | Cohen .................. A61K 9/0019 514/626 |
| 2010/0183625 A1 | 7/2010 | Sternlicht |
| 2011/0081411 A1 | 4/2011 | Perrett et al. |
| 2011/0160118 A1 | 6/2011 | Podolsky |
| 2011/0224176 A1 | 9/2011 | Dobak et al. |
| 2011/0294763 A1 * | 12/2011 | Dordunoo ............ A61K 9/0014 514/161 |
| 2012/0132204 A1 | 5/2012 | Lucking et al. |
| 2012/0164080 A1 | 6/2012 | Hill et al. |
| 2012/0213869 A1 | 8/2012 | Ma |
| 2012/0328671 A1 | 12/2012 | O'Neil et al. |
| 2013/0149345 A1 | 6/2013 | Lipp et al. |
| 2013/0165429 A1 | 6/2013 | Ray et al. |
| 2014/0371134 A1 | 12/2014 | Ray |
| 2014/0371179 A1 | 12/2014 | Simmons |
| 2015/0141515 A1 | 5/2015 | Stoltenberg et al. |

(Continued)

FOREIGN PATENT DOCUMENTS

| | | |
|---|---|---|
| JP | 10-109928 | 4/1998 |
| WO | 2006060027 | 6/2006 |
| WO | 2010109434 | 9/2010 |

OTHER PUBLICATIONS

Label for DIFLUCAN (Fluconazole Tablets), Distributed by Roerig, a Division of Pfizer, Mar. 2013 (35 pages).
Label (Package Insert) for Azithromycin, Distributed by SICOR Pharmaceuticals, Inc., Dec. 2016 (18 pages).
Label for BACTROBAN (mupirocin), Distributed by GlaxoSmithKline, Dec. 2015 (10 pages).
FDA Prescribing Information for NYSTATIN Powder, Distributed by Mayne Pharma, Summarized by www.drugs.com (5 pages).
PCCA, "New, Exclusive PCCA Base, XyliFos™: Boost the LoxaSperse™ Power in Nasal Nebulization and Decrease your Cost", Aug. 7, 2015 (2 pages).
Medinvent, LLC, "The NasoNeb Nasal Nebulizer," Nov. 15, 2013, document of 3 pages.
PCCA, XYIFOS Trademark Application No. 86642712, May 27, 2015, document of 8 pages.

(Continued)

*Primary Examiner* — Theodore R. West
(74) *Attorney, Agent, or Firm* — Akerman LLP

(57) ABSTRACT

A method of compounding a topical composition includes combining lidocaine and prilocaine, 2.5%/2.5%, cream, diclofenac sodium, 1.5%, topical solution, lidocaine hydrochloride, 4%, topical solution, diclofenac sodium USP powder, lidocaine hydrochloride USP monohydrate powder, and prilocaine hydrochloride USP powder and mixing to generate a cream.

11 Claims, 4 Drawing Sheets

(56) References Cited

U.S. PATENT DOCUMENTS

2015/0313836 A1  11/2015  Ray
2016/0166505 A1   6/2016  Ray

OTHER PUBLICATIONS

Lexington Podiatry, How to Make an Antifungal Foot Soak for Treatment of Foot Fungus, Feb. 27, 2011, document of 7 pages.
Roerig, "Diflucan-fluconazole tablet, Diflucan-fluconazole powder, for suspension," Pfizer, Mar. 2013, document of 61 pages.
Pfizer, "Fluconazole Injection, USP, in INTRAVIA Plastic Container," Pfizer Injectables, Aug. 2010, document of 4 pages, https://www.pfizer.com/files/products/uspi_fluconazole.pdf.
PCCA, "LoxaSperse™, Powder Excipient Base for Use in Nebulization and Irrigation Compounds," 2013, document of 3 pages.
Muraki et al. (2009) Inhaled montelukast inhibits cysteinyl-leukotriene-induced bronchoconstriction in ovalbumin-sensitized guinea-pigs: the potential as a new asthma medication. Int Immunopharmacol. 9(11):1337-1341. (Abstract Only).
Nascimento et al. (2011) Topical betamethasone and hyaluronidase in the treatment of phimosis in boys: a double-blind, randomized, placebo-controlled trial. Int Braz J Urol. 37(3):314-319.
Nichols et al. (2012) Safety and efficacy of topical azithromycin ophthalmic solution 1.0% in the treatment of contact lens-related dry eye. Eye Contact Lens. 38(2):73-79.
Nilfroushzadeh et al. (2009) Clindamycin lotion alone versus combination lotion of clindamycin phosphate plus tretinoin versus combination lotion of clindamycin phosphate plus salicylic acid in the topical treatment of mild to moderate acne vulgaris: a randomized control trial. Indian J Dermatol Venereol Leprol. 75(3):279-282.
O'Brien et al. (1995) Efficacy of ofloxacin vs cefazolin and tobramycin in the therapy for bacterial keratitis. Report from the Bacterial Keratitis Study Research Group. Arch Ophthalmol. 113(10):1257-1265. (Abstract Only).
Omidvari et al. (2007) Topical betamethasone for prevention of radiation dermatitis. Indian J Dermatol Venereol Leprol. 73(3):209. (Abstract Only).
Panahi et al. (2011) Doxepin cream vs betamethasone cream for treatment of chronic skin lesions due to sulfur mustard. Skinmed. 9(3):152-158. (Abstract Only).
Panda et al. (1996) Topical fluconazole therapy of Candida keratitis. Cornea. 15(4):373-375. (Abstract Only).
Pazoki-Toroudi et al. (2011) Combination of azelaic acid 5% and clindamycin 2% for the treatment of acne vulgaris. Cutan Ocul Toxicol. 30(4):286-291. (Abstract Only).
Philip et al. (2010) A phase I randomized, placebo-controlled, dose-exploration study of single-dose inhaled montelukast in patients with chronic asthma. J Asthma. 47(10):1078-1084. (Abstract Only).
Philip et al. (2011) The efficacy and tolerability of inhaled montelukast plus inhaled mometasone compared with mometasone alone in patients with chronic asthma. J Asthma. 48(5):495-502. (Abstract Only).
Pradeep et al. (2008) Clinical and microbiologic effects of subgingivally delivered 0.5% azithromycin in the treatment of chronic periodontitis. J Periodontol. 79(11):2125-2135. (Abstract Only).
Prevost et al. (2007) Palliative treatment of fingernail lichen planus. J Drugs Dermatol. 6(2):202-204. (Abstract Only).
Saraceno et al. (2014) Efficacy and maintenance strategies of two-compound formulation calcipotriol and betamethasone dipropionate gel (Xamiol® gel) in the treatment of scalp psoriasis: results from a study in 885 patients. J Dermatolog Treat. 25(1):30-33. (Abstract Only).
Scadding (2000) Other anti-inflammatory uses of intranasal corticosteroids in upper respiratory inflammatory diseases. Allergy. 55 Suppl 62:19-23.
Scheinfeld, (2008) Pruritic urticarial papules and plaques of pregnancy wholly abated with one week twice daily application of fluticasone propionate lotion: a case report and review of the literature. Dermatol Online J. 14(11):4.
Sharma et al. (2013) Comparative evaluation of topical versus intrastromal voriconazole as an adjunct to natamycin in recalcitrant fungal keratitis. Ophthalmology. 120(4):677-681.
Ship et al. (2007) Safety and effectiveness of topical dry mouth products containing olive oil, betaine, and xylitol in reducing xerostomia for polypharmacy-induced dry mouth. J Oral Rehabil. 34(10):724-732.
Sholapurkar et al. (2009) Comparison of efficacy of fluconazole mouthrinse and clotrimazole mouthpaint in the treatment of oral candidiasis. Aust Dent J. 54(4):341-346.
Silverman et al. (2003) Episodic viral wheeze in preschool children: effect of topical nasal corticosteroid prophylaxis. Thorax. 58(5):431-434.
Tai et al. (2013) Nasal carriage of *Staphylococcus aureus* in patients undergoing Mohs micrographic surgery is an important risk factor for postoperative surgical site infection: a prospective randomised study. Australas J Dermatol. 54(2):109-114. (Abstract Only).
Thorild et al. (2006) Caries in 4-year-old children after maternal chewing of gums containing combinations of xylitol, sorbitol, chlorhexidine and fluoride. Eur Arch Paediatr Dent. 7(4):241-245. (Abstract Only).
Ulff (2013) A potent steroid cream is superior to emollients in reducing acute radiation dermatitis in breast cancer patients treated with adjuvant radiotherapy. A randomised study of betamethasone versus two moisturizing creams. Radiother Oncol. 108(2):287-292. (Abstract Only).
Vander Salm et al. (1989) Reduction of sternal infection by application of topical vancomycin. J Thorac Cardiovasc Surg. 98(4):618-622. (Abstract Only).
Vural et al. (2003) The effect of topical fluticasone on nasal nitric oxide levels in a patient with allergic rhinitis. Ear Nose Throat J. 82(8):592-597. (Abstract Only).
Wu et al. (2013) An integrated analysis of the efficacy of fluticasone furoate nasal spray versus placebo on the nasal symptoms of perennial allergic rhinitis. Allergy Asthma Proc. 34(3):283-291. (Abstract Only).
Yactayo-Miranda et al. (2009) A prospective study determining the efficacy of topical 0.5% levofloxacin on bacterial flora of patients with chronic blepharoconjunctivitis. Graefes Arch Clin Exp Ophthalmol. 247(7):993-998.
Yim et al. (2010) Study to compare the efficacy and safety of fluconazole cream with flutrimazole cream in the treatment of superficial mycosis: a multicentre, randomised, double-blind, phase III trial. Mycoses. 53(6):522-529. (Abstract Only).
Yoon et al. (2007) Therapeutic effect of intracameral amphotericin B injection in the treatment of fungal keratitis. Cornea. 6(7):814-818. (Abstract Only).
FDA Prescribing Information for CLOBETASOL Ointment, Distributed by Taro Pharmaceuticals U.S.A., Inc., Apr. 2014, document of 8 pages.
FDA Prescribing Information for FLUOCINONIDE Cream, Distributed by Taro Pharmaceuticals U.S.A., Inc., Aug. 2012, document of 7 pages.
FDA Prescribing Information for ECONAZOLE NITRATE Cream, Distributed by Taro Pharmaceuticals U.S.A., Inc., Sep. 2014, document of 4 pages.
PCCA, "Itraconazole 5%/Fluticasone Propionate 1% Spira-Wash™ Gel," PCCA Formula 10291, May 18, 2012, document of 3 pages.
Hong et al., (2014) Comparison of analgesic effect of preoperative topical diclofenac and ketorolac on postoperative pain after photorefractive keratectomy. J Cataract Refract Surg. 40(10):1689-1696.
Predel et al., (2012) Efficacy and safety of diclofenac diethylamine 2.32% gel in acute ankle sprain. Med Sci Sports Exerc. 44(9):1629-1636.
Barthel et al., (2009) Randomized controlled trial of diclofenac sodium gel in knee osteoarthritis. Semin Arthritis Rheum. 39(3):203-212.
Segatto et al., (2013) Comparative study of actinic keratosis treatment with 3% diclofenac sodium and 5% 5-fluorouracil. An Bras Dermatol. 88(5):732-738.

(56) References Cited

OTHER PUBLICATIONS

Akarsu et al., (2011) Comparison of topical 3% diclofenac sodium gel and 5% imiquimod cream for the treatment of actinic keratoses. Clin Exp Dermatol. 36(5):479-484.
Peniston et al., (2012) Long-term tolerability of topical diclofenac sodium 1% gel for osteoarthritis in seniors and patients with comorbidities. Clin Interv Aging. 7:517-523.
Sankar et al., "Local drug delivery for oral mucosal diseases: challenges and opportunities," Oral Diseases, 2011, vol. 17, Supplement 1, pp. 73-84.
Solares et al., "Treatment of chronic rhinosinusitis exacerbations due to methicillin-resistant *Staphylococcus aureus* with mupirocin irrigations," American Journal of Otolaryngology—Head and Neck Medicine and Surgery, 2006, vol. 27, pp. 161-165.
Uren et al., Nasal Lavage With Mupirocin for the Treatment of Surgically Recalcitrant Chronic Rhinosinusitis, Laryngocope, 2008, vol. 118, pp. 1677-1680.
Arora et al., (2011) Voriconazole versus natamycin as primary treatment in fungal corneal ulcers. Clin Experiment Ophthalmol. 39(5):434-440.
Aykut et al., (2010) Mupirocin application at the exit site in peritoneal dialysis patients: five years of experience. Ren Fail. 32(3):356-361. (Abstract Only).
Bai et al., (2010) Short-term comparative study of the effects of preserved and unpreserved topical levofloxacin on the human ocular surface. Cutan Ocul Toxicol. 29(4):247-253. (Abstract Only).
Barikbin et al., (2009) Pimecrolimus 1% cream versus betamethasone 17-valerate 0.1% cream in the treatment of facial discoid lupus erythematosus: a double-blind, randomized pilot study. Clin Exp Dermatol. 34(7):776-780. (Abstract Only).
Barker et al., (1995) Oral care with vancomycin paste for reduction in incidence of alpha-hemolytic streptococcal sepsis. J Pediatr Hematol Oncol. 17(2):151-155. (Abstract Only).
Bassiri-Jahromi et al., (2012) A comparative evaluation of combination therapy of fluconazole 1% and urea 40% compared with fluconazole 1% alone in a nail lacquer for treatment of onychomycosis: therapeutic trial. J Dermatolog Treat. 23(6):453-456. (Abstract Only).
Bleecker et al., (2012) Once-daily fluticasone furoate is efficacious in patients with symptomatic asthma on low-dose inhaled corticosteroids. Ann Allergy Asthma Immunol. 109(5):353-358. (Abstract Only).
Cagle et al., (1981-1982) Topical tobramycin and gentamicin sulfate in the treatment of ocular infections: multicenter study. Curr Eye Res. 1(9):523-534. (Abstract Only).
Camacho et al., (2002) Oral and topical L-phenylalanine, clobetasol propionate, and UVA/sunlight—a new study for the treatment of vitiligo. J Drugs Dermatol. 1(2):127-131. (Abstract Only).
Carr et al., (2012) Comparison of intranasal azelastine to intranasal fluticasone propionate for symptom control in moderate-to-severe seasonal allergic rhinitis. Allergy Asthma Proc. 33(6):450-458. (Abstract Only).
Chang et al., (2012) A randomized, double-blind, placebo-controlled, pilot study to assess the efficacy and safety of clindamycin 1.2% and tretinoin 0.025% combination gel for the treatment of acne rosacea over 12 weeks. J Drugs Dermatol. 11(3):333-339. (Abstract Only).
Cherian et al., (2013) Oral antibiotics versus topical decolonization to prevent surgical site infection after Mohs micrographic surgery—a randomized, controlled trial. Dermatol Surg. 39(10):1486-1493. (Abstract Only).
Chiambaretta et al., (2008) Tear concentrations of azithromycin following topical administration of a single dose of azithromycin 0.5%, 1.0%, and 1.5% eyedrops (T1225) in healthy volunteers. Eur J Ophthalmol. 18(1):13-20.
Clareus et al., (2009) The DESIRE study—psoriasis patients' satisfaction with topical treatment using a fixed combination of calcipotriol and betamethasone dipropionate in daily clinical practice. Eur J Dermatol. 19(6):581-585. (Abstract Only).

Colin et al., (2003) Corneal penetration of levofloxacin into the human aqueous humour: a comparison with ciprofloxacin. Acta Ophthalmol Scand. 81(6):611-613.
Comstock et al., (2012) Safety and tolerability of loteprednol etabonate 0.5% and tobramycin 0.3% ophthalmic suspension in pediatric subjects. Paediatr Drugs. 14(2):119-130.
Corradini et al., (2006) Amphotericin B and lysine acetylsalicylate in the combined treatment of nasal polyposis associated with mycotic infection. J Investig Allergol Clin Immunol. 16(3):188-193.
Dehghani et al., (2009) Cefazolin-Gentamicin versus Vancomycin-Ceftazidime Eye Drops for Bacterial Corneal Ulcers;a Randomized Clinical Trial. J Ophthalmic Vis Res. 4(1):19-23.
Denis et al., (2008) Microbiological efficacy of 3-day treatment with azithromycin 1.5% eye-drops for purulent bacterial conjunctivitis. Eur J Ophthalmol. 18(6):858-868.
Dransfield et al., (2013) Once-daily inhaled fluticasone furoate and vilanterol versus vilanterol only for prevention of exacerbations of COPD: two replicate double-blind, parallel-group, randomised controlled trials. Lancet Respir Med. 1(3):210-223. (Abstract Only).
Du Bois et al., (1999) Randomized trial of inhaled fluticasone propionate in chronic stable pulmonary sarcoidosis: a pilot study. Eur Respir J. 13(6):1345-1350. (Abstract Only).
Epstein et al., (2002) Fluconazole mouthrinses for oral candidiasis in postirradiation, transplant, and other patients. Oral Surg Oral Med Oral Pathol Oral Radiol Endod. 93(6):671-675. (Abstract Only).
Fadlallah et al., (2012) Azithromycin 1.5% ophthalmic solution: efficacy and treatment modalities in chronic blepharitis. Arq Bras Oftalmol. 75(3):178-182.
Feldman et al., (2009) Topical clobetasol propionate in the treatment of psoriasis: a review of newer formulations. Am J Clin Dermatol. 10(6):397-406.
Findlay et al., (2013) Increased peritoneal dialysis exit site infections using topical antiseptic polyhexamethylene biguanide compared to mupirocin: results of a safety interim analysis of an open-label prospective randomized study. Antimicrob Agents Chemother. 57(5):2026-2028.
drugbank.com, Fluticasone Propionate—Accession No. DB00588, (2015) Available at http://www.drugbank.ca/drugs/DB00588, document of 17 pages.
Flynn et al., (1995) Oropharyngeal candidiasis in immunocompromised children: a randomized, multicenter study of orally administered fluconazole suspension versus nystatin. The Multicenter Fluconazole Study Group. J Pediatr. 127(2):322-328. (Abstract Only).
Fowler et al., (2002) A randomized double-blind study to compare the effects of nasal fluticasone and betamethasone on the hypothalamo-pituitary-adrenal axis and bone turnover in patients with nasal polyposis. Clin Otolaryngol Allied Sci. 27(6):489-493. (Abstract Only).
Gallenga et al., (1999) Topical lomefloxacin 0.3% twice daily versus tobramycin 0.3% in acute bacterial conjunctivitis: A multicenter double-blind phase III study. Ophthalmologica. 213(4):250-257. (Abstract Only).
Giavina-Bianchi et al., (2008) Fluticasone furoate nasal spray in the treatment of allergic rhinitis. Ther Clin Risk Manag. 4(2):465-472.
Goldberg et al., (2002) The use of otic powder in the treatment of acute external otitis. Am J Otolaryngol. 23(3):142-147. (Abstract Only).
Grossman et al., (1993) Fluticasone propionate aqueous nasal spray is safe and effective for children with seasonal allergic rhinitis. Pediatrics. 92(4):594-599. (Abstract Only).
Grove et al., (2013) Tolerability and irritation potential of four topical acne regimens in healthy subjects. J Drugs Dermatol. 12(6):644-649. (Abstract Only).
Howland et al. (1996) The efficacy of fluticasone propionate aqueous nasal spray for allergic rhinitis and its relationship to topical effects. Clin Ther. 18(6):1106-1117. (Abstract Only).
Howland, (1996) Fluticasone propionate: topical or systemic effects? Clin Exp Allergy. 26 Suppl 3:18-22. (Abstract Only).
Jarratt et al., (2012) Efficacy and safety of clindamycin-tretinoin gel versus clindamycin or tretinoin alone in acne vulgaris: a randomized, double-blind, vehicle-controlled study. J Drugs Dermatol. 11(3):318-326. (Abstract Only).

(56) References Cited

OTHER PUBLICATIONS

Keith, (2012) Fluticasone furoate nasal spray reduces symptoms of uncomplicated acute rhinosinusitis: a randomised placebo-controlled study. Prim Care Respir J. 21(3):267-275.
Khodaeiani et al., (2013) Topical 4% nicotinamide vs. 1% clindamycin in moderate inflammatory acne vulgaris. Int J Dermatol. 52(8):999-1004. (Abstract Only).
Laforce et al., (2013) Ocular safety of fluticasone furoate nasal spray in patients with perennial allergic rhinitis: a 2-year study. Ann Allergy Asthma Immunol. 111(1):45-50. (Abstract Only).
Lalitha et al., (2014) In vitro susceptibility of filamentous fungal isolates from a corneal ulcer clinical trial. Am J Ophthalmol. 157(2):318-326.
Mahdy et al., (2010) Topical amphotericin B and subconjunctival injection of fluconazole (combination therapy) versus topical amphotericin B (monotherapy) in treatment of keratomycosis. J Ocul Pharmacol Ther. 26(3):281-285. (Abstract Only).
Man et al., (2013) The effect of intranasal fluticasone propionate irrigations on salivary cortisol, intraocular pressure, and posterior subcapsular cataracts in postsurgical chronic rhinosinusitis patients. Int Forum Allergy Rhinol. 3(12):953-957. (Abstract Only).
McHugh et al., (2004) A topical azithromycin preparation for the treatment of acne vulgaris and rosacea. J Dermatolog Treat. 15(5):295-302. (Abstract Only).
Meltzer, (1997) The pharmacological basis for the treatment of perennial allergic rhinitis and non-allergic rhinitis with topical corticosteroids. Allergy. 52(36 Suppl):33-40.
Milgrom et al., (2009) Xylitol pediatric topical oral syrup to prevent dental caries: a double-blind randomized clinical trial of efficacy. Arch Pediatr Adolesc Med. 163(7):601-607.
Mino De Kaspar et al., (2008) A prospective randomized study to determine the efficacy of preoperative topical levofloxacin in reducing conjunctival bacterial flora. Am J Ophthalmol. 145(1):136-142.
Miura et al., (2009) Topical clindamycin in post-adenotonsillectomy analgesia in children: a double-blind, randomized clinical trial. Otolaryngol Head Neck Surg. 141(4):509-515. (Abstract Only).
Enander Malmros et al., (1990) Plasma concentrations and analgesic effect of EMLA (lidocaine/prilocaine) cream for the cleansing of leg ulcers. Acta Derm Venereol. 1990;70(3):227-30. (Abstract Only).
Cousins et al., (2013) The safety and efficacy of KAI-1678—an inhibitor of epsilon protein kinase C (εPKC)-versus lidocaine and placebo for the treatment of postherpetic neuralgia: a crossover study design. Pain Med. Apr. 2013;14(4):533-40.
Sabatowski et al., (2012) Safety and efficacy outcomes of long-term treatment up to 4 years with 5% lidocaine medicated plaster in patients with post-herpetic neuralgia. Curr Med Res Opin. Aug. 2012;28(8):1337-46.
Wasner et al., (2005) Postherpetic neuralgia: topical lidocaine is effective in nociceptor-deprived skin. J Neurol. Jun. 2005;252(6):677-86. (Abstract Only).
Campbell et al., Systemic absorption of topical lidocaine in normal volunteers, patients with post-herpetic neuralgia, and patients with acute herpes zoster. J Pharm Sci. May 2002;91(5):1343-50. (Abstract Only).
Tajti et al., Topical acetylsalicylic acid versus lidocaine for postherpetic neuralgia: results of a double-blind comparative clinical trial. Neurobiology (Bp). 1999;7(2):103-8. (Abstract Only).
Rowbotham et al., (1995) Topical lidocaine gel relieves postherpetic neuralgia. Ann Neurol. 37(2):246-253. (Abstract Only).
"4% Xylocaine®-MPF (Lidocaine HCL) Sterile Solution" prescribing information, APP Pharmaceuticals, LLC (Feb. 2010).
Kanai et al., "Efficacy of a Metered-dose 8% Lidocaine Pump Spray for Patients with Post-herpetic Neuralgia," Pain Med. 10(4), 902-09 (2009).
Predel et al. (2013) A randomized, double-blind, placebo-controlled multicentre study to evaluate the efficacy and safety of diclofenac 4% spray gel in the treatment of acute uncomplicated ankle sprain. J Int Med Res. 41(4):1187-1202.
Simon et al., (2009) Efficacy and safety of topical diclofenac containing dimethyl sulfoxide (DMSO) compared with those of topical placebo, DMSO vehicle and oral diclofenac for knee osteoarthritis. Pain. 143(3):238-245.
Moen, (2009) Topical diclofenac solution. Drugs. 69(18):2621-2632.
Roth et al., (2011) Diclofenac sodium topical solution 1.5% w/w with dimethyl sulfoxide compared with placebo for the treatment of osteoarthritis: pooled safety results. Postgrad Med. Nov. 2011;123(6):180-8. (Abstract Only).
Taylor et al, (2011) Safety profile of topical diclofenac: a meta-analysis of blinded, randomized, controlled trials in musculoskeletal conditions. Curr Med Res Opin. Mar. 2011;27(3):605-22. (Abstract Only).
Baraf et al., (2011) Safety and efficacy of topical diclofenac sodium gel for knee osteoarthritis in elderly and younger patients: pooled data from three randomized, double-blind, parallel-group, placebo-controlled, multicentre trials. Drugs Aging. Jan. 1, 2011;28(1):27-40. (Abstract Only).
Predel et al., (2013) Efficacy and safety of diclofenac diethylamine 1.16% gel in acute neck pain: a randomized, double-blind, placebo-controlled study. BMC Musculoskelet Disord. Aug. 21, 2013;14:250.
González De Vega et al., (2013) Traumeel vs. diclofenac for reducing pain and improving ankle mobility after acute ankle sprain: a multicentre, randomised, blinded, controlled and non-inferiority trial. Int J Clin Pract. Oct. 2013;67(10):979-89.
Ahmed et al., (2015) Effect of 1.5% Topical Diclofenac on Clinical Neuropathic Pain. Anesthesiology. Jul. 2015;123(1):191-8.
Derry et al, (2012) Topical NSAIDs for chronic musculoskeletal pain in adults. Cochrane Database Syst Rev. Sep. 12, 2012;(9):CD007400.
Derry et al., (2015) Topical NSAIDs for acute musculoskeletal pain in adults. Cochrane Database Syst Rev. Jun. 11, 2015;(6):CD007402.
Yan et al., (2014) Can diclofenac ester prodrug promote direct penetration across the skin? Journal of Chemical and Pharmaceutical Research, 6(7):2701-2713.
Singer et al., (2015) Topical NSAIDs effect on corneal sensitivity. Cornea May 2015;34(5):541-3.
Wadsworth et al., (2016) Efficacy and safety of diclofenac sodium 2% topical solution for osteoarthritis of the knee: a randomized, double-blind, vehicle-controlled, 4 week study. Curr Med Res Opin. 2016;32(2):241-50.
Alañón et al., (2014) Comparison between topical anaesthesia with cocaine versus lidocaine plus adrenaline for outpatient laser dacryocystorhinostomy. Arch Soc Esp Oftalmol. 89(2):53-57.
Kwon et al., (2012) Treatment for postoperative wound pain in gynecologic laparoscopic surgery: topical lidocaine patches. J Laparoendosc Adv Surg Tech A. 22(7):668-673.
Christensen et al., (2013) Lidocaine analgesia for removal of wound vacuum-assisted closure dressings: a randomized double-blinded placebo-controlled trial. J Orthop Trauma. 27(2):107-112.
Lee et al., (2013) The effect of buffered lidocaine in local anesthesia: a prospective, randomized, double-blind study. J Hand Surg Am. 38(5):971-975.
Gaviola et al., (2013) A prospective, randomized, double-blind study comparing the efficacy of topical anesthetics in nasal endoscopy. Laryngoscope. 123(4):852-858.
Coudert et al., (2014) Phase III, randomized, double-blind, placebo-controlled trial of topical 2 % lidocaine for the prevention and treatment of oral mucosal pain in children. Clin Oral Investig. 18(4):1189-1194.
Nayak et al. (2006) Evaluation of three topical anaesthetic agents against pain: a clinical study. Indian J Dent Res. 17(4):155-160.
Wolff et al., (2011) 5% lidocaine-medicated plaster vs other relevant interventions and placebo for post-herpetic neuralgia (PHN): a systematic review. Acta Neurol Scand. May 2011;123(5):295-309.
Nalamachu et al., (2006) A comparison of the lidocaine patch 5% vs naproxen 500 mg twice daily for the relief of pain associated with carpal tunnel syndrome: a 6-week, randomized, parallel-group study. MedGenMed. Aug. 9, 2006;8(3):33.
Ernst et al., (1995) Lidocaine adrenaline tetracaine gel versus tetracaine adrenaline cocaine gel for topical anesthesia in linear scalp and facial lacerations in children aged 5 to 17 years. Pediatrics. Feb. 1995;95(2):255-8. (Abstract Only).

(56) References Cited

OTHER PUBLICATIONS

Kanai et al., (2010) Lidocaine eye drops attenuate pain associated with ophthalmic postherpetic neuralgia. May 1, 2010;110(5):1457-60.
Zink et al., (2011) Lidocaine patches reduce pain in trauma patients with rib fractures. Am Surg. Apr. 2011;77(4):438-42. (Abstract Only).
Taddio et al., (2002) Lidocaine-prilocaine cream versus tetracaine gel for procedural pain in children. Ann Pharmacother. 36(4):687-692. (Abstract Only).
Ingalls et al., (2010) Randomized, double-blind, placebo-controlled trial using lidocaine patch 5% in traumatic rib fractures. J Am Coll Surg. Feb. 2010;210(2):205-9. (Abstract Only).
Kanai et al., (2009) The analgesic effect of a metered-dose 8% lidocaine pump spray in posttraumatic peripheral neuropathy: a pilot study. Anesth Analg. Mar. 2009;108(3):987-91. (Abstract Only).
Khaliq et al., (2007) Topical lidocaine for the treatment of postherpetic neuralgia. Cochrane Database Syst Rev. Apr. 18, 2007;(2):CD004846. (Abstract Only).
Tornblom-Paulander et al., (2015) Novel topical formulation of lidocaine provides significant pain relief for intrauterine device insertion: pharmacokinetic evaluation and randomized placebo-controlled trial. Fertil Steril. Feb. 2015,103(2):422-7.
Samarai et al., (2014) Pupil dilation with intra-cameral lidocaine versus topical midriatics during phacoemulsification. Glob J Health Sci. Sep. 18, 2014;6(7 Spec No):8-12.
Farrington et al., (2015) Pain management prior to nasogastric tube placement: atomized lidocaine. ORL Head Neck Nurs. 2015 Winter;33(1):8-16. (Abstract Only).
Cohen et al., (2014) Topical lidocaine gel with and without subconjunctival lidocaine injection for intravitreal injection: a within-patient study. Ophthalmic Surg Lasers Imaging Retina. Jul.-Aug. 2014;45(4):306-10.
Hizli et al., (2015) Novel approach for pain control in patients undergoing prostate biopsy: iliohypogastric nerve block with or without topical application of prilocaine-lidocaine: a randomized controlled trial. Urol J. Feb. 22, 2015;12(1):2014-9.
Shamra et al., (2015) Is Nebulized Lidocaine Adequate Topical Anesthesia for Diagnostic Transnasal Tracheoscopy? Ann Otol Rhinol Laryngol. Jul. 2015;124(7):545-9. (Abstract Only).
Kaur et al., (2015) A Randomized Trial of 1% vs 2% Lignocaine by the Spray-as-You-Go Technique for Topical Anesthesia During Flexible Bronchoscopy. Chest. Sep. 2015;148(3):739-45.
Zempsky et al., (1997) EMLA versus TAC for topical anesthesia of extremity wounds in children. Ann Emerg Med. Aug. 1997;30(2):163-6. (Abstract Only).
Claeys et al., (2011) Management of pain associated with debridement of leg ulcers: a randomized, multicentre, pilot study comparing nitrous oxide-oxygen mixture inhalation and lidocaïne-prilocaïne cream. J Eur Acad Dermatol Venereol. Feb. 2011;25(2):138-44. (Abstract Only).
Avramidis et al., (2000) Reduction in pain associated with open carpal tunnel decompression. J Hand Surg Br. Apr. 2000;25(2):147-9. (Abstract Only).
Khan et al., (2014) Efficacy of combination of 0.2% GTN and lignocaine ointments in wound healing and pain relief after Milligan Morgan hemorrhoidectomy—a comparison with lignocaine and 0.2% GTN ointments separately. Int J Surg. 2014;12(4):329-33.
Minassian et al, (2002) Randomized trial of lidocaine ointment versus placebo for the treatment of postpartum perineal pain. Obstet Gynecol. Dec. 2002;100(6):1239-43 (Abstract Only).
Singer et al., (2001) LET versus EMLA for pretreating lacerations: a randomized trial. Acad Emerg Med. Mar. 2001;8(3):223-30.
Lok et al., (1999) EMLA cream as a topical anesthetic for the repeated mechanical debridement of venous leg ulcers: a double-blind, placebo-controlled study. J Am Acad Dermatol. Feb. 1999;40(2 Pt 1):208-13. (Abstract Only).
Hansson et al.,(1993) Repeated treatment with lidocaine/prilocaine cream (EMLA) as a topical anaesthetic for the cleansing of venous leg ulcers. A controlled study. Acta Derm Venereol. Jun. 1993;73(3):231-3. (Abstract Only).
Mattsson et al., (1999) Digital image analysis of erythema development after experimental thermal injury to human skin: effect of postburn topical local anesthetics (EMLA). Anesth Analg. May 1999;88(5):1131-6. (Abstract Only).
Liang et al., (2011) Topical anesthetic EMLA for postoperative wound pain in stereotactic gamma knife radiosurgery: a perspective, randomized, placebo-controlled study. Minim Invasive Neurosurg. Apr. 2011;54(2):75-8.
Descroix et al., (2011) Efficacy of topical 1% lidocaine in the symptomatic treatment of pain associated with oral mucosal trauma or minor oral aphthous ulcer: a randomized, double-blind, placebo-controlled, parallel-group, single-dose study. J Orofac Pain. 2011 Fall;25(4):327-32. (Abstract Only).
Rosenthal et al., (2001) Using a topical anaesthetic cream to reduce pain during sharp debridement of chronic leg ulcers. J Wound Care. Jan. 2001;10(1):503-5. (Abstract Only).

* cited by examiner

COMPOUNDED COMPOSITIONS AND METHODS FOR TREATING PAIN

CROSS-REFERENCE TO RELATED APPLICATIONS

This patent application a continuation-in-part of U.S. patent application Ser. No. 16/010,731, filed Jun. 18, 2018, which is a divisional of U.S. patent application Ser. No. 15/354,630 filed Nov. 17, 2016, now U.S. Pat. No. 9,999,604. U.S. patent application Ser. Nos. 16/010,731 and 15/354,630 are hereby incorporated by reference herein.

TECHNICAL FIELD

The present application relates to compounded medications. In particular, the present application relates to compounded topical compositions comprising lidocaine, prilocaine, diclofenac, xylitol, and/or poloxamers and methods of making and using such compounded topical compositions.

BACKGROUND

Pain is often treated with medication such as anti-inflammatory or local anesthetic drugs. Treatment can include administration of the medication via oral, intramuscular, subcutaneous, intravenous, and topical routes.

Diclofenac sodium topical solution is a non-steroidal anti-inflammatory drug (NSAID) indicated for the treatment of signs and symptoms of osteoarthritis of the knee. For the relief of such signs and symptoms, the recommended dose of diclofenac sodium topical solution, 1.5% (w/w), is 40 drops on each painful knee, 4 times a day.

Lidocaine hydrochloride topical solution is a local anesthetic agent indicated for the production of topical anesthesia of accessible mucous membranes of the oral and nasal cavities and proximal portions of the digestive tract. When used as a spray, or when applied by cotton applicators or packs, as when instilled into a cavity, the suggested dosage of Lidocaine Hydrochloride Topical Solution, 4%, is 1 to 5 mL (40 to 200 mg lidocaine HCl), i.e., 0.6 to 3 mg/kg or 0.3 to 1.5 mg/lb. body weight. When spraying, the solution is to be transferred from its original container to an atomizer.

Lidocaine and prilocaine cream, 2.5%/2.5% is a eutectic mixture of lidocaine 2.5% and prilocaine 2.5% formulated as an oil in water emulsion and is indicated for use on normal intact skin for local analgesia and genital mucous membranes for superficial minor surgery and as pretreatment for infiltration anesthesia. The cream is applied to intact skin under occlusive dressing to provide dermal analgesia by the release of lidocaine and prilocaine from the cream into the epidermal and dermal layers of the skin and by the accumulation of lidocaine and prilocaine in the vicinity of dermal pain receptors and nerve endings.

SUMMARY

In one aspect, a method of compounding a topical composition includes combining lidocaine and prilocaine, 2.5%/2.5%, cream, diclofenac sodium, 1.5%, topical solution, lidocaine hydrochloride, 4%, topical solution, diclofenac sodium USP powder, lidocaine hydrochloride USP monohydrate powder, and prilocaine hydrochloride USP powder and mixing to generate a cream.

In one embodiment, the method includes combining xylitol, poloxamer, or both. In a further or another example, the method may include combining one or more parabens. One or more parabens may include methylparaben, propylparaben, or both.

In one embodiment, the method includes combining a thickening agent. In one example, the diclofenac sodium, 1.5%, topical solution, is combined in an amount such that the cream comprises between about 20% and approximately 50% by weight diclofenac sodium, 1.5%, topical solution, and the lidocaine and prilocaine, 2.5%/2.5%, cream is combined in an amount such that the cream comprises at least 50% by weight lidocaine and prilocaine, 2.5%/2.5%, cream. In a further example, the lidocaine hydrochloride, 4%, topical solution is combined in an amount such that the cream comprises between approximately 1% and approximately 7% by weight lidocaine hydrochloride, 4%, topical solution, the diclofenac sodium USP powder is combined in an amount such that the cream comprises between approximately 0.5% and approximately 5% by weight diclofenac sodium USP powder, the lidocaine hydrochloride USP monohydrate powder is combined in an amount such that the cream comprises between 0.75% and approximately 5% by weight lidocaine hydrochloride USP monohydrate powder, and the prilocaine hydrochloride USP powder is combined in an amount such that the cream comprises between 0.75% and approximately 5% by weight prilocaine hydrochloride USP powder. In a further example, the method includes combining at least one of methylparaben or propylparaben. Xylitol, poloxamer, or both may also be included. In one example, the cream includes approximately 1.5% by weight diclofenac sodium, approximately 2.5% by weight lidocaine, and approximately 2.5% by weight prilocaine. In one example, the method may further include combining a thickening agent in an amount between approximately 1% and approximately 5% by weight of the cream. In one formulation, the thickening agent comprises hydroxyethyl cellulose.

In another aspect, a compounded topical cream may be produced by a process comprising combining lidocaine and prilocaine, 2.5%/2.5%, cream, diclofenac sodium, 1.5%, topical solution, lidocaine hydrochloride, 4%, topical solution, diclofenac sodium USP powder, lidocaine hydrochloride USP monohydrate powder, and prilocaine hydrochloride USP powder and mixing to generate a cream.

In still another aspect, a topical pain cream may include between approximately 0.5% and approximately 5% by weight of a combination of xylitol and one or more poloxamers. The topical pain cream may also include one or more active drugs selected from analgesics, local anesthetics, NSAIDS, antidepressants, anticonvulsants, opioids, NMDA receptor antagonists, muscle relaxants, or combination thereof. In one embodiment, the one or more poloxamers comprise poloxamer 407 and poloxamer 188.

In yet another aspect, a method of compounding a topical pain cream includes combining lidocaine hydrochloride, 4%, topical solution, and a cream base or one or more cream base components and mixing the ingredients.

In one example, the cream base or one or more cream base components comprises a commercially available cream base for compounding. In another example, the cream base or one or more cream base components comprises a commercially available medicated cream. In another example, the cream base or one or more cream base components comprises all or a portion of an oil phase. The cream base or one or more cream base components may further comprises an emulsifier and a thickening agent.

In one example, the lidocaine hydrochloride, 4%, topical solution is combined in an amount approximately 1% to approximately 7% by weight of the compounded topical cream. Combining the ingredients may further include combining one or more active drugs selected from an analgesics, local anesthetics, NSAIDS, antidepressants, anticonvulsants, opioids, NMDA receptor antagonists, muscle relaxants, or combination thereof.

The above-described and other features and advantages of the present disclosure will be appreciated and understood by those skilled in the art from the following detailed description, drawings, and appended claims.

DESCRIPTION

Figure 1A:
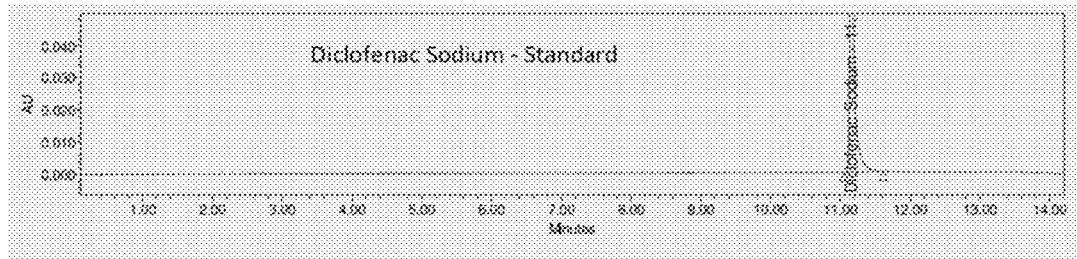
FIGS. 1A-1E are exemplary chromatograms of standard, untreated, heat treated, acid treated (45° C.), and acid treated (65° C.) Diclofenac Sodium samples, respectively, generated in a degradation study according to various embodiments described herein.

The present embodiments may relate to topically delivered or deliverable compounded compositions including topical solutions of compounded medications for treatment of various ailments, such as inflammation or pain.

The compounded medications may typically include topical solutions that may be topically administered at a body surface.

A compounded topical composition may comprise one or more compounded topical solutions. In various embodiments, the compounded composition may include at least two active agents including a local anesthetic and a Non-Steroidal Anti-Inflammatory Drug (NSAID). The compounded topical composition may include all or some of the active agents in a commercially available medicated aqueous solution. In one embodiment, a compounded topical composition comprises a compounded formulation comprising one or more commercially available medicated solutions and a commercially available medicated cream. For example, the compounded topical composition may comprise a NSAID solution and/or a commercially available local anesthetic solution compounded with a commercially available medicated cream comprising a local anesthetic. Such a compounded topical composition may be stably formulated for topical delivery to treat various ailments, such as inflammation or pain. Thus, the compounded medications may include topical solutions, emulsions, ointments, creams, lotions, or gels that may be topically administered at a body surface. In one embodiment, a compounded topical composition for the effective administration of multiple medications simultaneously for treatment of one or more ailments may be provided.

In one embodiment, a compounded topical solution for the effective administration of multiple medications simultaneously for treatment of one or more ailments may be provided. The compounded topical solution may include at least two active agents including a local anesthetic and a Non-Steroidal Anti-Inflammatory Drug (NSAID). The compounded topical solution may include all or some of the active agents in aqueous solution. In some embodiments, the topical solution comprises a compounded topical solution comprising at least two commercially available topical solutions that are compounded together. For example, a compounded topical solution may include a commercially available NSAID topical solution and a commercially available local anesthetic topical solution. In some embodiments, the compounded topical solution may further include multiple local anesthetics or NSAIDs obtained from commercially available solutions, commercially available creams, bulk powders, ground tablets, or combination thereof of such local anesthetics or NSAIDS.

In one embodiment, the compounded topical solution includes additional active agents selected from one or more anticonvulsants, nerve depressants, muscle relaxants, NMDA (N-Methyl-D-aspartate) receptor antagonists, opiate or opioid agonists, antidepressants, and/or other active agents.

The compounded topical solutions may be topically applied via any suitable mode of administration of the solution for the ailment treated, including, e.g., spray, drops, atomizer, wash, swab, sponge, absorbent dressing, instillation or irrigation. Ailments treated may include conditions such as inflammation, rheumatoid arthritis, osteoarthritis, lateral epicondylitis (tennis elbow), medial epicondylitis (golfer's elbow), chondromalacia patellae—CMP (runner's knee), tendonitis/carpel tunnel, soft tissue pain, fibromyalgia, diabetic neuropathy, peripheral neuropathy, neck pain, back pain, localized pain, plantar fasciitis, achilles tendonitis, tarsal tunnel-post-op massage, or heel pain. The compounded topical solution may exhibit excellent storage characteristics, and avoid separation and/or degradation of the active ingredients in the aqueous environment for substantial lengths of time.

As introduced above, the compounded topical solution may include a NSAID topical solution compounded with a local anesthetic topical solution. The NSAID component of the topical compounded solution may act to block the synthesis of prostaglandins by inhibiting cyclooxygenase-2 and cyclooxygenase-1, for example. In various embodiments, the NSAID may be selected from one or more salicylic acid derivatives (e.g., aspirin, diflunisal, salsalate, trilisate), one or more propionic acids (e.g., flurbiprofen, ibuprofen, ketoprofen, naproxen, oxaprozin), one or more acetic acids (e.g., diclofenac, etodolac, indomethacin, ketorolac, nabumetone, sulindac, tolmetin), one or more fenamates (e.g., meclofenamate), one or more oxicams (meloxicam, piroxicam), or one or more COX-2 inhibitors (e.g., celecoxib, rofecoxib, valdecoxib), or combinations thereof. For example, in one embodiment, the NSAID topical solution comprises a benzeneacetic acid derivative such as diclofenac or pharmaceutically acceptable salt thereof provided in an aqueous solution. In various embodiments, the local anesthetic may be selected from lidocaine, prilocaine, benzocaine, or combination thereof. The local anesthetic may be provided in an aqueous solution and compounded with the NSAID topical solution. One or both of the NSAID topical solution or the local anesthetic topical solution may be commercially available topical solutions. For example, the NSAID topical solution may include a commercially available diclofenac, or pharmaceutically acceptable salt thereof, topical solution and the local anesthetic topical solution may include a commercially available lidocaine, or pharmaceutically acceptable salt thereof, topical solution. In embodiments including one or more additional NSAIDs, local anesthetics, or both, the additional actives may be provided in commercially available solutions, creams, or pure powders or crushed commercial tablets and then combined with the compounded topical solution or a component thereof.

In various embodiments, the compounded topical solution may include a diclofenac topical solution comprising diclofenac in an aqueous solution. The diclofenac topical solution may be a commercially available diclofenac topical solution, such as diclofenac sodium solution for topical administration. The diclofenac sodium solution may contain, for example, 1.5% (w/w), diclofenac sodium wherein each 1 mL of solution contains approximately 16.05 mg of diclofenac sodium. In one embodiment, the diclofenac solution comprises a diclofenac sodium solution, 1.5% (w/w), such as that which is manufactured under the trade name PENNSAID® by Nuvo Manufacturing, Varennes, Quebec, Canada or Diclofenac Sodium Topical Solution, 1.5% (w/w), manufactured by Apotex Inc. Toronto, Ontario, Canada M9L 1T9 for Apotex Corp. Weston, Fla. 33326 for treating the pain of osteoarthritis of the knee. The diclofenac solution may also contain various inactive ingredients such as dimethyl sulfoxide USP (DMSO, 45.5% w/w), ethanol, glycerin, propylene glycol and purified water. In one embodiment, the diclofenac solution comprises a diclofenac sodium solution marketed under the trade name PENNSAID® and manufactured by Nuvo Manufacturing, Varennes, Quebec, Canada, in a 2% (w/w) diclofenac solution for treating the pain of osteoarthritis of the knee. Each gram of solution may contain approximately 20 mg of diclofenac sodium and various inactive ingredients such as dimethyl sulfoxide USP (DMSO, 45.5% w/w), ethanol, purified water, propylene glycol, and hydroxypropyl cellulose. In other embodiments, other concentrations of diclofenac solution, such as diclofenac sodium solutions, may be used.

In various embodiments, the compounded topical solution may include a lidocaine topical solution comprising lidocaine in an aqueous solution. The lidocaine topical solution may be a commercially available lidocaine topical solution, such as lidocaine hydrochloride solution for topical administration. The lidocaine hydrochloride solution may contain, for example, 4% lidocaine (w/v) wherein each mL includes 40 mg lidocaine HCl. For example, in one embodiment, the lidocaine topical solution may be Lidocaine Hydrochloride Topical Solution USP, 4% manufactured by IGI Labs, Inc., Buena, N.J., in 50 mL screw cap glass bottles. The lidocaine hydrochloride topical solution may contain various inactive ingredients such as methylparaben, purified water, and sodium hydroxide to adjust pH to 6.0-7.0.

The compounded topical solution formulated by combining a lidocaine hydrochloride topical solution and diclofenac sodium topical solution may include relatively low concentrations of the active ingredients compared to conventional topical formulations including one or more of the active ingredients. Due to the formulation and combination described herein, the present compounded topical solution may provide similar effectiveness while having an increased safety profile. The increased safety profile may be especially beneficial to patients with gastric bleeds, on blood thinners, etc. The compounded composition may also provide local anesthetics benefits while promoting deeper penetration into the skin and leveraging DMSO in the diclofenac sodium solution embedded into the compounded topical cream, e.g., 45.5% (w/w) of the diclofenac sodium solution compounded with the lidocaine hydrochloride solution.

In various embodiments, the compounded topical solution comprises diclofenac or diclofenac sodium at a concentration between 0.1% and 1.9% and lidocaine or lidocaine hydrochloride at a concentration of between 0.1% and 3.9%. In one example, the compounded topical solution includes approximately 0.5% or more, approximately 1.0% or more, or approximately 1.45% or more diclofenac or diclofenac sodium and approximately 0.2% or more, approximately 0.28% or more, or approximately 0.3% or more lidocaine or lidocaine hydrochloride. As used herein, the term approximately means +/−10% of the stated value it modifies. In some embodiments, the compounded topical solution includes between approximately 1.0% and approximately 1.9%, approximately 1.1% and approximately 1.8%, approximately 1.2% and approximately 1.7%, approximately 1.2% and approximately 1.6%, approximately 1.2% and approximately 1.5%, approximately 1.2% and approximately 1.4%, approximately 1.2% and approximately 1.3%, approximately 1.3% and approximately 1.6%, approximately 1.3% and approximately 1.5%, approximately 1.3% and approximately 1.4%, approximately 1.4% and approximately 1.6%, approximately 1.4% and approximately 1.5% (w/v) diclofenac or diclofenac sodium and between approximately 1.0%, approximately 0.2% and approximately 0.8%, approximately 0.2% and approximately 0.7%, approximately 0.2% and approximately 0.6%, approximately 0.2% and approximately 0.5%, approximately 0.2% and approximately 0.4%, approximately 0.2% and approximately 0.3%, approximately 0.3% and approximately 0.7%, approximately 0.3% and approximately 0.6%, approximately 0.3% and approximately 0.5%, approximately 0.3% and approximately 0.4%, approximately 0.330% and approximately 0.340% (w/v) lidocaine or lidocaine hydrochloride. For example, in various embodiments, the compounded topical solution comprises between approximately 1.0% and approximately 2.0%, such as between approximately 1.3% and approximately 1.6%, (w/v) diclofenac sodium and between approximately 0.1% and approximately 0.5%, such as between approximately 0.3% and approximately 0.35%, (w/v) lidocaine hydrochloride. In one embodiment, the compounded topical solution includes approximately 1.47% (w/v) diclofenac sodium and approximately 0.333% (w/v) lidocaine hydrochloride. In another embodiment, the compounded topical solution includes approximately 1.35% (w/v) diclofenac and approximately 0.4% (w/v) lidocaine. In various embodiments, a method of formulating the compounded topical solution includes combining a commercially available diclofenac sodium solution, diclofenac sodium topical solution, 1.5% (w/w), or diclofenac sodium topical solution 2.0% (w/w) solution, with a commercially available lidocaine solution, such as lidocaine hydrochloride topical solution, 4%, to form a compounded topical solution having one of the above listed concentrations (w/v) of diclofenac sodium and lidocaine hydrochloride. Stronger or weaker concentrations of diclofenac or diclofenac sodium topical solutions and lidocaine or lidocaine hydrochloride topical solutions may be used wherein the amounts of such solutions added are modified to achieve the appropriate w/v concentrations.

In various embodiments, the compounded topical solution comprises a commercially available diclofenac sodium topical solution, 1.5% (w/w), compounded with a commercially available lidocaine hydrochloride topical solution, 4%, wherein the compounded topical solution includes diclofenac sodium topical solution, 1.5% (w/w), at a concentration between 0.1% and 99%, such as between 50% and 95%, (v/v) and lidocaine hydrochloride topical solution, 4%, at a concentration between 0.1% and 90%, such as 0.2% and 5%, (v/v). In one example, the compounded topical solution includes approximately 80% or more, approximately 90% or more, or approximately 91.7% (v/v) diclofenac sodium topical solution, 1.5% (w/w), and approximately 4% or more, approximately 7% or more, or approximately 8.32% (v/v) lidocaine hydrochloride topical solution, 4%. In one embodiment, the compounded topical solution includes approximately 90% (v/v) diclofenac sodium topical solution, 1.5% (w/w), and approximately 10% (v/v) lidocaine hydrochloride topical solution, 4%. In some embodiments, the compounded topical solution includes between approximately 50% and approximately 98%, approximately 55% and approximately 97%, approximately 60% and approximately 96%, approximately 70% and approximately 95%, approximately 80% and approximately 95%, approximately 85% and approximately 95%, approximately 90% and approximately 95%, approximately 90% and approximately 94%, approximately 90% and approximately 93%, approximately 90% and approximately 92%, approximately 91% and approximately 93%, approximately 91% and approximately 92% (v/v) diclofenac sodium topical solution, 1.5% (w/w), and between approximately 2% and approximately 20%, approximately 4% and approximately 18%, approximately 6% and approximately 16%, approximately 6% and approximately 16%, approximately 6% and approximately 12%, approximately 6% and approximately 10%, approximately 7% and approximately 14%, approximately 7% and approximately 12%, approximately 7% and approximately 10%, approximately 8% and approximately 14%, approximately 8% and approximately 12%, approximately 8% and approximately 10% (v/v) lidocaine hydrochloride topical solution, 4%. For example, in various embodiments, the compounded topical solution comprises between approximately 80% and approximately 95%, such as between approximately 90% and approximately 93% (v/v) diclofenac sodium topical solution, 1.5% (w/w), and between approximately 4% and approximately 14%, such as between approximately 7% and approximately 10% (v/v) lidocaine hydrochloride topical solution, 4%. In one embodiment, the compounded topical solution includes approximately 91.7% diclofenac sodium and approximately 8.32% lidocaine hydrochloride topical solution, 4%. In various embodiments, a method of formulating the compounded topical solution includes combining a commercially available diclofenac sodium solution, such as diclofenac sodium topical solution, 1.5% (w/w), with a commercially available lidocaine solution, such as lidocaine hydrochloride topical solution, 4%, to form a compounded topical solution having one of the above listed concentrations (v/v) of diclofenac sodium topical solution, 1.5% (w/w), and lidocaine hydrochloride topical solution, 4%. Stronger or weaker concentrations of diclofenac or diclofenac sodium topical solutions and lidocaine or lidocaine hydrochloride topical solutions may be used wherein the amounts of such solutions added are modified to achieve the appropriate v/v concentrations.

As introduced above, a method of making a compounded topical solution may include combining, e.g., adding to each other, two commercially available topical solutions. The method may further include mixing the two combined solutions to form a compounding topical solution for administration of multiple active agents. Example 1 presents a method of making a compounded topical solution that includes approximately 1.47% diclofenac sodium (w/v) and approximately 0.333% (w/v) lidocaine hydrochloride. However, the method may be applied to make compounded topical solutions having other active concentrations, such as those described herein.

EXAMPLE 1—Diclofenac Sodium/Lidocaine HCl Compounded Topical Solution 1.47/0.333%

Diclofenac sodium topical solution, 1.5% (w/w), and lidocaine hydrochloride topical solution, 4%, were compounded to make a compounded topical solution. Appropriate amounts of diclofenac sodium topical solution, 1.5% (w/w), and lidocaine hydrochloride topical solution, 4%, were measured. Diclofenac sodium topical solution, 1.5% (w/w), includes approximately 16.05 mg diclofenac sodium per mL. Accordingly, approximately 0.9167 mL of diclofenac sodium topical solution, 1.5% (w/w), was measured for every mL of compounded topical solution. Approximately 0.0832 mL of lidocaine hydrochloride topical solution, 4%, was measured for every mL of compounded topical solution. The measured ingredients where combined in a beaker. The beaker was placed on a magnetic stirring plate and a stir bar was placed in the beaker and rotated at a speed to create a small vortex for 5 minutes. The stirred solution was then placed in containers. Each mL of the compounded topical solution included approximately 91.7% (v/v) diclofenac sodium topical solution, 1.5% (w/w), and approximately 8.32% lidocaine hydrochloride topical solution, 4%.

Table I below depicts potency test results for the compounded topical solution of Example 1. Potency was determined via USP <621> HPLC, USP<851> Spectrophotometry, and specific monograph, using a High Performance Liquid Chromatography with an Ultraviolet/Photodiode Array Detector.

TABLE I

Potency Test

| Analyte | Reported | Measured | Test Potency | Test Method |
|---|---|---|---|---|
| Lidocaine Hydrochloride | 0.333% | 0.336% | 101% | HPLC with an Ultraviolet/photodiode array |
| Diclofenac Sodium | 1.47 | 1.51% | 103% | HPLC |

The compounded topical solution or derivative thereof may be topically applied to a body surface utilizing for example, spray, drops, atomizer, wash, swab, sponge, absorbent dressing, instillation or irrigation. Topical application may be with respect to body surfaces such as trunk, limbs, hands, feet, neck, head, cavities, etc. In various embodiments, the compounded topical solution may find orthopedic application, e.g., as part of a therapeutic treatment of rheumatoid arthritis/osteoarthritis, lateral epicondylitis (tennis elbow), medial epicondylitis (golfer's elbow), chondromalacia patellae—CMP (runner's knee), or tendonitis/carpel tunnel; rheumatologic application, e.g., as part of a therapeutic treatment of soft tissue pain, fibromyalgia, diabetic neuropathy, peripheral neuropathy, rheumatoid arthritis, or osteoarthritis; neurologic application, e.g., as part of a therapeutic treatment diabetic neuropathy, peripheral neuropathy, fibromyalgia, or localized pain; podiatric application, e.g., as part of a therapeutic treatment of diabetic neuropathy, peripheral neuropathy, plantar fasciitis, Achilles tendonitis, tarsal tunnel—post-op massage, or heel pain—which may include usage in conjunction with urea; pain management application, e.g., as part of a therapeutic treatment of soft tissue pain, fibromyalgia, diabetic/peripheral neuropathy, rheumatoid arthritis, osteoarthritis, or neck and back pain; or ear nose and throat or dental applications, e.g., as part of a therapeutic treatment of temporomandibular joint disorder (TMJD or TMJ), or trigeminal neuralgia.

The present disclosure also includes a stability-indicating method for the analysis of compounded solutions. As presented in the following example forced degradation study performed on a compounded solution preparation comprising Diclofenac Sodium/Lidocaine HCl Solution 1.47%/0.333%, the methods used are stability-indicating. The methods described below and similar may be used to establish stability-indicating methods for analysis of other compounded solutions using similarly designed forced degradation studies.

At least two degradation conditions may be used to determine specificity. In the exemplary protocol, two degradation conditions, heat and acid, were used. With respect to the heat degradation condition, 1 gram samplings of the preparation were heated at 40° C., 65° C., and 80° C. At day 2, day 6, and day 8 the treated samples were taken out and analyzed. With respect to the acid degradation condition, 120 uL of 0.1N HCl was added to 1 gram samplings of the preparation. The acid degradation treated samplings were then either kept at room temperature or heated at 40° C. and 65° C. At day 2, day 6, and day 8, the treated samplings were taken out and analyzed. Acid degradation condition also included 0.333 mL of sample incubated with 0.333 mL of concentrated sulfuric acid at 40° C. and 65° C. These treated samples where then analyzed after 14 hours and 18 hours of incubation. The 0.333 mL samples were prepared for analysis by dilution to 50 mL with methanol. Samplings of the heat and acid treated preparations were treated the same way. Lidocaine standard was prepared by accurately weighing and dissolving Lidocaine Hydrochloride USP Monohydrate (PCCA, C169931) in Methanol to a final concentration of 100 µg/mL. Diclofenac standard was prepared by accurately weighing and dissolving Diclofenac Sodium USP (PCCA, C164795) in Methanol to a similar final concentration.

Standards and samples for were analyzed with a gradient method on a Waters Acquity UPLC equipped with a PDA detector. Eluent A was prepared by adding 1 mL of Trifluoroacetic acid to 1 L of DI Water. Eluent B was prepared by adding 1 mL of Trifluoroacetic acid to 1 L of Acetonitrile. The flow rate was 1 mL per minute. The column temperature was 50° C. The injection volume was 2 uL. The sample tray was kept at 22° C. The LC column was Acclaim RSLC PA2 Polar Advantage II, 2.2 um 120 A 2.1×150 mm from Thermo Scientific. The analysis time was 14 minutes with an additional 1 minute delay. The gradient was set as described in Table II. The processing wavelengths were 225 nm for Lidocaine and 276 nm for Diclofenac Sodium.

TABLE II

Gradient Used for Analysis of Standards and Samples

| Minutes | Eluent A % | Fluent B % |
|---|---|---|
| 0 | 98.0 | 2.0 |
| 6 | 88.0 | 12.0 |
| 13 | 20.0 | 80.0 |
| 13.2 | 98.0 | 2.0 |

Figure 1B:
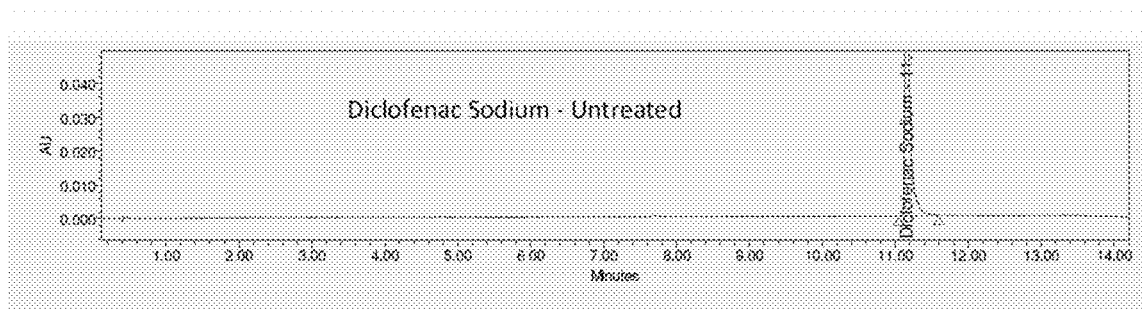
Figure 1C:
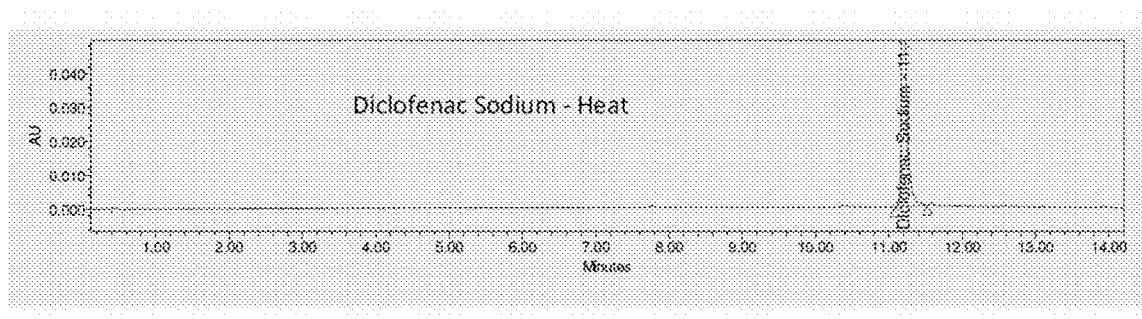
Figure 1D:
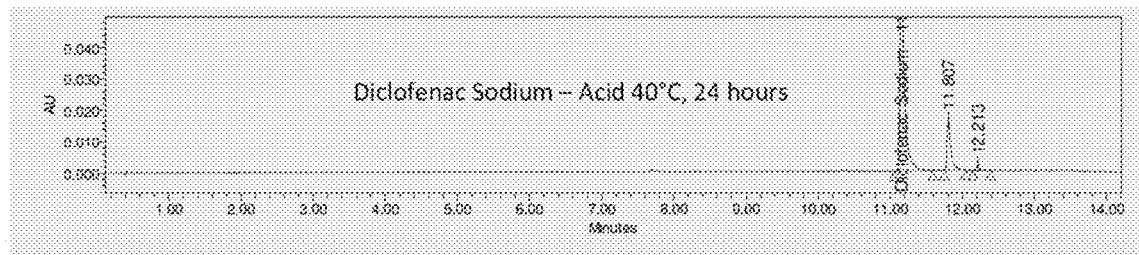
Figure 1E:
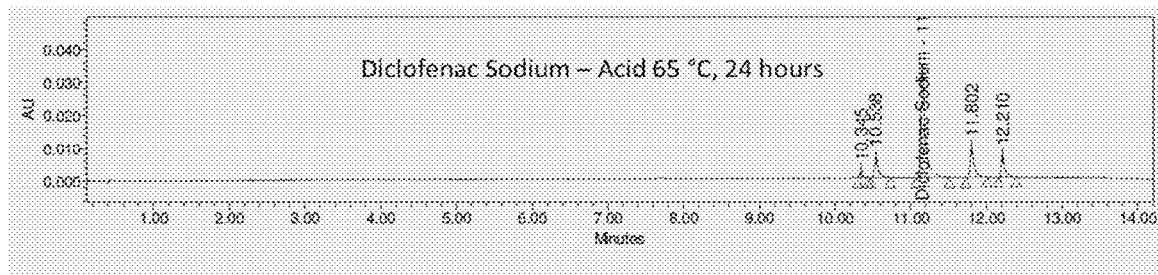

Percent recoveries of Diclofenac Sodium for untreated and treated samples are shown in Table III. FIGS. 1A-1E present exemplary chromatograms of standard, untreated, heat treated, acid treated at 45° C., and acid treated at 65° C. Diclofenac Sodium samples, respectively. Retention time for Diclofenac Sodium is at 11.5 minutes.

TABLE III

Recovery of Diclofenac Sodium (%)

| | Day 0 | Day 2 | Day 6 | Day 8 |
|---|---|---|---|---|
| Untreated | 103 | 104 | 104 | 104 |
| 40° C. | | 106 | 103 | 105 |
| 65° C. | | 106 | 101 | 103 |
| 80° C. | | 99.6 | 95.6 | 89.4 |
| H+, RT | | 86.3 | 63.3 | 57.0 |
| H+, 40° C. | | 70.8 | 44.5 | 28.0 |
| H+, 65° C. | | 33.3 | 0.0 | 0.0 |

RT = 22-25° C.

Figure 2A:
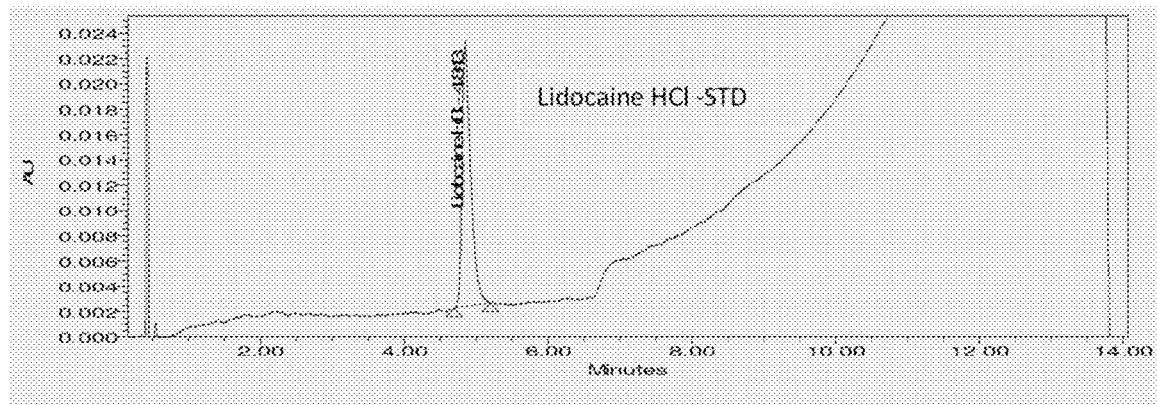
FIGS. 2A-2D are exemplary chromatograms of standard, untreated, heat treated, and acid treated Lidocaine HCl samples, respectively, generated in a degradation study according to various embodiments described herein.
Figure 2B:
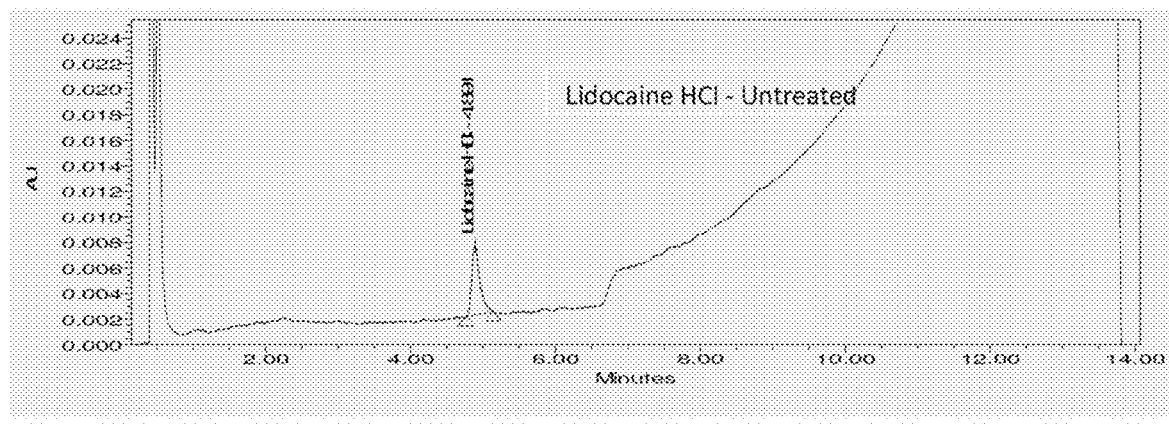
Figure 2C:
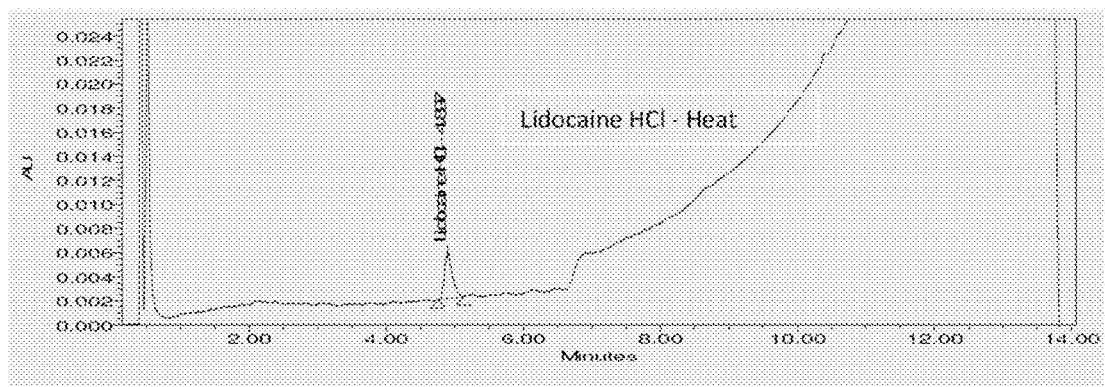
Figure 2D:
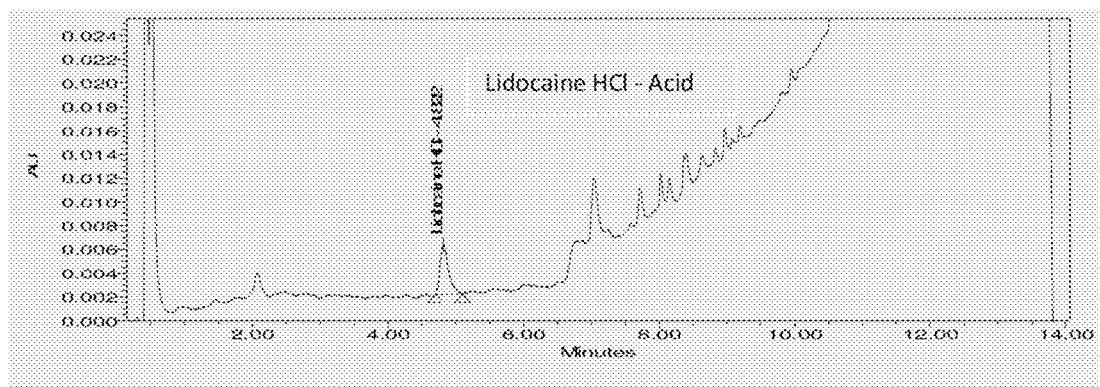

Percent recoveries of Lidocaine HCl for untreated and treated samples are shown in Table IV. FIGS. 2A-2D present exemplary chromatograms of standard, untreated, heat treated, and an acid treated Lidocaine HCl samples, respectively. Retention time for Lidocaine HCl is at 4.89 minutes.

TABLE IV

Recovery of Lidocaine HCl (%)

| | Day 0 | Day 2 | Day 6 | Day 8 |
|---|---|---|---|---|
| Untreated | 101 | 101 | 102 | 104 |
| 40° C. | | 100 | 99.4 | 104 |
| 65° C. | | 108 | 94.5 | 97.5 |
| 80° C. | | 96.0 | 99.9 | 75.6 |
| H+, RT | | 98.5 | 96.5 | 101 |
| H+, 40° C. | | 101 | 103 | 96.4 |
| H+, 65° C. | | 97.0 | 102 | 101 |

RT = 22-25° C.

Percent recoveries of Lidocaine HCl for sulfuric acid treated samples are shown in Table V.

TABLE V

Recovery of Lidocaine HCl (%)

| | 14 Hours | 18 Hours |
|---|---|---|
| Control | 102 | 102 |
| H2SO4, 40° C. | 96.3 | 75.4 |
| H2SO4, 65° C. | 86.2 | 73.9 |

The above degradation study performed for Diclofenac Sodium and Lidocaine HCl Solution in Diclofenac Sodium/Lidocaine HCl Solution 1.47%/0.333% shows no co-elution or interference between degradants and API in all samples (stressed and untreated), thus, it demonstrates specificity. The methods used for this study are therefore stability-indicating methods.

In further embodiments, the method may also include combining one or more additional active agents comprising one or more additional NSAIDs selected from salicylic acid derivatives (e.g., aspirin, diflunisal, salsalate, trilisate), one or more propionic acids (e.g., flurbiprofen, ibuprofen, ketoprofen, naproxen, oxaprozin), one or more acetic acids (e.g., etodolac, indomethacin, ketorolac, nabumetone, sulindac, tolmetin), one or more fenamates (e.g., meclofenamate), one or more oxicams (meloxicam, piroxicam), or one or more COX-2 inhibitors (e.g., celecoxib, rofecoxib, valdecoxib), or combinations thereof, one or more additional local anesthetics selected from prilocaine, benzocaine, or combination thereof, one or more muscle relaxants selected from baclofen, carisoprodol, orphenadrine, cyclobenzaprine, dantrolene, tizanidine, amitriptyline, or combinations thereof, one or more NMDA receptor antagonists such as ketamine, or one or more opioid or opiate agonists selected from oxycodone, morphine, fentanyl, hydrocodone, codeine, butalbital, tramadol, or combinations thereof, one or more nerve depressants selected from gabapentin, topiramate, lamotrigine, or combinations thereof, and/or other active agents. The additional active agents may be provided in powder form (e.g., pure powder or crushed tablets), suspension, gel, solution, or cream, e.g., emulsion. The additional active agents may comprise 0.1% to 5% (w/v) of the compounded topical solution.

In further embodiments, the compounded topical solution may be further compounded with a cream to form a compounded cream for topic al/transdermal administration. Cream is used generally herein to include a cream, hydrous ointment, lotion, gel, or emulsion (oil in water or water in oil). Creams, lotions, and gels are typically "water containing" and/or emulsions. Creams and lotions have similar appearance while creams are typically thicker. Gels are typically clear. In some embodiments, the compounded topical solution is compounded with a commercially available cream, which may or may not include additional active agents.

In some embodiments, the compounded topical composition comprises a topical pain cream comprising at least two commercially available topical solutions that are compounded together. For example, a compounded topical composition may include a commercially available NSAID topical solution and a commercially available local anesthetic topical solution as described herein. The compounded topical composition may also comprise medicated creams, lotions, gels, ointments, pastes, tablets, bulk powders, or other medicated formats including all or a portion of one or more of the active agents. Thus, the compounded topical composition may include a local anesthetic agent comprising one or more local anesthetics and an NSAID agent comprising one or more NSAIDs obtained from commercially available solutions, creams, lotions, gels, ointments, pastes, ground oral tablets, or combination thereof. Some embodiments may also include bulk powders. For example, the topical composition may comprise a compounded topical composition comprising at least two commercially available medicated topical solutions, a commercially available medicated topical cream (which may include a cream, hydrous ointment, lotion, gel, or emulsion) or anhydrous ointment, and one or more actives comprising bulk powder or ground tablets.

In one embodiment, the compounded topical composition includes one or more additional active agents selected from one or more anticonvulsants, nerve depressants, muscle relaxants, NMDA (N-Methyl-D-aspartate) receptor antagonists, opiate or opioid agonists, antidepressants, and/or other active agents. However, some embodiments may exclude additional active agents.

The compounded topical composition may be topically applied for treatment of an ailment, e.g., by topically contacting the composition to skin or mucosal surfaces such as by spreading or layering. In one example, an occlusive dressing may be applied. As noted above and elsewhere herein ailments treated may include conditions such as inflammation, rheumatoid arthritis, osteoarthritis, lateral epicondylitis (tennis elbow), medial epicondylitis (golfer's elbow), chondromalacia patellae—CMP (runner's knee), tendonitis/carpel tunnel, soft tissue pain, fibromyalgia, diabetic neuropathy, peripheral neuropathy, neck pain, back pain, localized pain, plantar fasciitis, achilles tendonitis, tarsal tunnel—post-op massage, or heel pain. The compounded topical composition may exhibit excellent storage characteristics, and avoid separation and/or degradation of the active ingredients for substantial lengths of time. As noted above, the composition may be in a cream format comprising an aqueous phase and an oil phase. In various embodiments, active ingredients may be in the aqueous phase, oil phase, or both.

The compounded topical composition may include an NSAID agent as described above and elsewhere herein. For example, the NSAID agent may be selected from one or more salicylic acid derivatives (e.g., aspirin, diflunisal, salsalate, trilisate), one or more propionic acids (e.g., flurbiprofen, ibuprofen, ketoprofen, naproxen, oxaprozin), one or more acetic acids (e.g., diclofenac, etodolac, indomethacin, ketorolac, nabumetone, sulindac, tolmetin), one or more fenamates (e.g., meclofenamate), one or more oxicams (meloxicam, piroxicam), or one or more COX-2 inhibitors (e.g., celecoxib, rofecoxib, valdecoxib), or combinations thereof. For example, in one embodiment, the NSAID agent comprises a benzeneacetic acid derivative such as diclofenac or pharmaceutically acceptable salt thereof.

The local anesthetic agent may comprise one or more local anesthetics selected from lidocaine, prilocaine, benzocaine, or combination thereof. All or a portion of the local anesthetic agent may be provided in a commercially available aqueous solution. Additionally or alternatively, all or a portion of the local anesthetic agent may be provided by a commercially available medicated cream (e.g., cream, hydrous ointment, gel, lotion, emulsion) or anhydrous ointment. In some of the above embodiments, the local anesthetic agent may also include bulk powder, ground oral tablets, or both. For example, an NSAID topical solution may include a commercially available diclofenac, or pharmaceutically acceptable salt thereof, topical solution and a local anesthetic topical solution may include a commercially available lidocaine, or pharmaceutically acceptable salt thereof, topical solution. In embodiments including one or more additional NSAIDs, local anesthetics, or both, additional actives may be provided in commercially available solutions, creams, or bulk/pure powders or crushed commercial tablets and then combined with the compounded topical composition or a component thereof. For example, one or more additional local anesthetic and/or NSAID actives may be provided in a solution, cream, ointment, bulk/pure powder, or crushed commercial tablet. The compounded topical composition may also be supplemented with creams, bulk/pure powders, or crushed commercial tablets comprising an NSAID and/or local anesthetic that is also present in a commercial topical solution compounded to formulate the topical compounded topical composition.

In various embodiments, the compounded topical composition may include a diclofenac topical solution comprising diclofenac sodium in an aqueous solution. Diclofenac sodium topical solution is a medicated topical solution indicated for the treatment of signs and symptoms of osteoarthritis of the knee. The diclofenac topical solution may be a commercially available diclofenac topical solution, such as diclofenac sodium solution for topical administration. The diclofenac sodium solution may contain, for example, 1.5% (w/w), diclofenac sodium wherein each 1 mL of solution contains approximately 16.05 mg of diclofenac sodium. The diclofenac solution may also contain various inactive ingredients such as dimethyl sulfoxide USP (DMSO, 45.5% w/w), ethanol, glycerin, propylene glycol and purified water. In other embodiments, other concentrations of diclofenac solution, such as diclofenac sodium solutions, may be used.

In various embodiments, the compounded topical composition may include diclofenac bulk powder, such as diclofenac sodium or diclofenac potassium bulk powder. In a further or another example, the compounded topical composition includes crushed diclofenac sodium tablets for oral administration containing diclofenac sodium. The tablets may also include one or more of aluminum hydrate, colloidal silicon dioxide, hypromellose, lactose monohydrate, magnesium stearate, microcrystalline cellulose, polyethylene glycol, polysorbate 80, polyvinyl acetate phthalate, propylene glycol, silica, sodium alginate, sodium starch glycolate (Type A), stearic acid, synthetic black iron oxide, talc, or titanium dioxide. In a further or another example, the compounded topical composition includes diclofenac sodium topical gel including diclofenac sodium. Diclofenac sodium topical gel may also contain one or more of carbomer homopolymer Type C, cocoyl caprylocaprate, fragrance, isopropyl alcohol, mineral oil, polyoxyl 20 cetostearyl ether, propylene glycol, purified water, or strong ammonia solution. Diclofenac sodium topical gel may be available as Diclofenac Sodium Topical Gel, 1% w/w. In an above or further example, the compounded topical composition may include diclofenac potassium for oral solution containing diclofenac potassium and which is available as a flavored soluble powder that is designed to be mixed with water prior to oral administration. In an above or further example, the compounded topical composition may include diclofenac potassium tablets for oral administration containing diclofenac potassium and which may also contain one or more of colloidal silicon dioxide, corn starch, FD&C Blue No. 2, FD&C Red No. 40, FD&C Yellow No. 6, hypromellose, lactose monohydrate, magnesium stearate, microcrystalline cellulose, polyethylene glycol 4000, povidone, sodium starch glycolate, titanium dioxide, or tricalcium phosphate.

In various embodiments, the compounded topical composition may include a lidocaine topical solution comprising lidocaine in an aqueous solution. The lidocaine topical solution may be a commercially available lidocaine topical solution, such as lidocaine hydrochloride solution for topical administration. The lidocaine hydrochloride topical solution may contain, for example, 4% lidocaine (w/v) wherein each mL includes 40 mg lidocaine hydrochloride. As noted above, the lidocaine hydrochloride topical solution may contain various inactive ingredients such as methylparaben, purified water, and sodium hydroxide to adjust pH to 6.0-7.0.

In one embodiment, the topical composition includes lidocaine bulk powder, such as lidocaine hydrochloride USP monohydrate powder in addition to or instead of lidocaine topical solution. Lidocaine hydrochloride USP monohydrate powder includes 1 g of lidocaine per 1.23 g.

Prilocaine is another local anesthetic drug that may be compounded with a NSAID and/or another local anesthetic to formulate the compounded topical composition, which may be compounded at least in part from one or more topical solutions such as diclofenac topical solution and/or lidocaine topical solution. Prilocaine may be compounded from prilocaine hydrochloride USP powder. Prilocaine hydrochloride USP powder includes 1 g of prilocaine per 1.165 g. In some embodiments, prilocaine may be compounded from Prilocaine Hydrochloride Injection, USP, 4%, which is a sterile, non-pyrogenic isotonic solution that contains prilocaine HCl at 40 mg/mL at a pH of 6.0 to 7.0 and is designed to be administered parenterally by injection. In an above or another embodiment, prilocaine may be compounded from Prilocaine Hydrochloride 4% with epinephrine injection, which is a sterile, non-pyrogenic isotonic solution that contains prilocaine with epinephrine (as bitartrate) and is administered parenterally by injection. The injection solution is available as prilocaine epinephrine 1:200,000, containing prilocaine HCl 40.0 mg/mL, epinephrine 0.005 mg/mL, citric acid 0.2 mg/mL, and sodium metabisulfite 0.5 mg/mL and has a pH of 3.3 to 5.5.

The compounded topical composition may be formulated by compounding one or more actives with a commercially available medicated composition, such as a solution, cream, or ointment, comprising two or more actives. For example, the compounded topical composition may include a lidocaine and prilocaine cream. In one example, the compounded topical composition includes Lidocaine 2.5% and Prilocaine 2.5% Cream, USP, (or Lidocaine and Prilocaine 2.5%/2.5% Cream) which is an emulsion in which the oil phase is a eutectic mixture of lidocaine and prilocaine in a ratio of 1:1 by weight. This eutectic mixture has a melting point below room temperature and therefore both local anesthetics exist as a liquid oil rather than as crystals. It is packaged in 5 gram and 30 gram tubes. Each gram of lidocaine and prilocaine cream contains lidocaine 25 mg, prilocaine 25 mg, polyoxyethylene fatty acid esters (as emulsifiers) such as PEG-60/hydrogenated castor oil, carboxypolymethylene (as a thickening agent) such as carbomer 934P, carbopol 5984, sodium hydroxide to adjust to a pH approximating 9, and purified water to 1 gram. Lidocaine 2.5% and Prilocaine 2.5% Cream, USP, is currently manufactured by Teligent Pharma, Inc., Buena, N.J. 08310 USA, for distribution by Actavis Pharma, Inc., Parsippany, N.J. 07054 USA. Lidocaine and prilocaine cream, 2.5%/2.5%, is also manufactured and distributed by other sources such as E. Fougera & Co. a division of Fougera Pharmaceuticals Inc., Melville, N.Y. 11747.

In some embodiments, the compounded topical composition includes a commercially available lidocaine and prilocaine periodontal gel, such as Periodontal Gel, 2.5%/2.5%, which is a microemulsion in which the oil phase is a eutectic mixture of lidocaine and prilocaine in a ratio of 1:1 by weight. This eutectic mixture has a melting point below room temperature; therefore, both local anesthetics exist as liquid oils rather than as crystals. Lidocaine and Prilocaine Gel 2.5%/2.5% is currently available under ORAQIX® (manufactured for Dentsply Pharmaceutical, York, Pa. 17404) in single-use glass cartridges that deliver up to 1.7 g (1.7 mL) of gel (42.5 mg of lidocaine and 42.5 mg of prilocaine). In various embodiments described herein including lidocaine and prilocaine cream, 2.5%/2.5%, lidocaine and prilocaine cream, 2.5%/2.5%, may be replaced in whole or in-part with Lidocaine and Prilocaine Gel 2.5%/2.5%.

In one embodiment, the compounded topical composition comprises a commercially available topical solution portion comprising a lidocaine hydrochloride solution and/or a diclofenac sodium solution and a lidocaine and prilocaine cream or gel, 2.5%/2.5% portion. For example, the compounded topical composition may comprise a diclofenac sodium topical solution and lidocaine and prilocaine cream, 2.5%/2.5%. In another example, the compounded topical composition comprises a commercially available diclofenac sodium solution, a commercially available lidocaine hydrochloride solution, and commercially available lidocaine and prilocaine cream, 2.5%/2.5%. In another or a further example, the compounded topical composition comprises diclofenac sodium USP powder, lidocaine hydrochloride USP monohydrate powder, prilocaine hydrochloride USP powder, or combination thereof. The actives present in one or more bulk powders may also be replaced or supplemented with powder obtained from ground oral tablets comprising the actives. The bulk powder or ground oral tablets may comprise pharmaceutically acceptable salts of the active agents, such as those identified herein. The commercially available diclofenac sodium solution may be diclofenac sodium topical solution, 1.5% (w/w). The lidocaine hydrochloride solution may be lidocaine hydrochloride topical solution, 4%.

In some embodiments, the compounded topical composition comprises a topical solution portion comprising diclofenac sodium topical solution, 1.5% (w/w), and lidocaine hydrochloride topical solution, 4%. The compounded topical composition may further comprise a lidocaine and prilocaine cream or gel, 2.5%/2.5% portion. The compounded topical composition may also comprise a powder portion comprising diclofenac, lidocaine, prilocaine, or combination thereof. The powder portion may comprise bulk powder or ground oral tablets. The powder portion may comprise pharmaceutically acceptable salts of the active agents, such as those identified herein.

In various embodiments, the compounded topical composition may comprise diclofenac sodium topical solution, 1.5% (w/w), in an amount between approximately 0.1 g and approximately 0.8 g per gram. For example, the topical composition may comprise between approximately 0.1 g and approximately 0.7 g, approximately 0.1 g and approximately 0.6 g, approximately 0.1 g and approximately 0.5 g, approximately 0.1 g and approximately 0.4 g, approximately 0.1 g and approximately 0.3 g, approximately 0.1 g and approximately 0.3 g, approximately 0.2 and approximately 0.8, approximately 0.2 g and approximately 0.7 g, approximately 0.2 g and approximately 0.6 g, approximately 0.2 g and approximately 0.5 g, approximately 0.2 g and approximately 0.4 g, approximately 0.2 and approximately 0.3 g, approximately 0.3 and approximately 0.8, approximately 0.3 g and approximately 0.7 g, approximately 0.3 g and approximately 0.6 g, approximately 0.3 g and approximately 0.5 g, approximately 0.3 g and approximately 0.4 g, approximately 0.4 and approximately 0.8, approximately 0.4 g and approximately 0.7 g, approximately 0.4 g and approximately 0.6 g, approximately 0.4 g and approximately 0.5 g, approximately 0.5 g and approximately 0.6 g, approximately 0.5 g and approximately 0.7 g, approximately 0.5 g and approximately 0.8 g, or greater than or equal to approximately 0.1 g, approximately 0.2 g, approximately 0.3 g, approximately 0.4 g, approximately 0.5 g, approximately 0.6 g, approximately 7 g, or approximately 0.8 g, or less than or equal to approximately 0.8 g, approximately 0.7 g, approximately 0.6 g, approximately 0.5 g, approximately 0.4 g, approximately 0.3 g, approximately 0.2 g, or approximately 0.1 g diclofenac sodium topical solution, 1.5% (w/w), per gram of compounded topical composition. In one example, the topical composition comprises approximately 0.1 g, approximately 0.2 g, approximately 0.3 g, approximately 0.4 g, approximately 0.5 g, approximately 0.6 g, approximately 0.7 g, or approximately 0.8 g diclofenac sodium topical solution, 1.5% (w/w), per gram.

In some methods, diclofenac sodium topical solution, 1.5% (w/w), or equivalent is compounded in an amount between approximately 0.1 g and approximately 0.8 g per gram or in a lesser amount sufficient to provide between approximately 1.6 mg and approximately 13 mg of the diclofenac sodium present in one gram of the compounded topical composition alone or together with one or more additional diclofenac sources, e.g. bulk powder or ground tablets. For example, diclofenac sodium topical solution, 1.5% (w/w), may be added in an amount sufficient to provide between approximately 1.6 mg and approximately 12 mg, approximately 2 mg and approximately 10 mg, approximately 2 mg and approximately 9 mg, approximately 2 mg and approximately 8 mg, approximately 2 mg and approximately 7 mg, approximately 2 mg and approximately 6 mg, approximately 2 mg and approximately 5 mg, approximately 2 mg and approximately 4 mg, approximately 2 mg and approximately 3 mg, approximately 3 mg and approximately 9 mg, approximately 3 mg and approximately 8 mg, approximately 3 mg and approximately 7 mg, approximately 3 mg and approximately 6 mg, approximately 3 mg and approximately 5 mg, approximately 4 mg and approximately 12 mg, approximately 4 mg and approximately 11 mg, approximately 4 mg and approximately 10 mg, approximately 4 mg and approximately 9 mg, approximately 4 mg and approximately 8 mg, approximately 4 mg and approximately 7 mg, approximately 4 mg and approximately 6 mg, approximately 4 mg and approximately 5 mg, approximately 5 mg and approximately 12 mg, approximately 5 mg and approximately 11 mg, approximately 5 mg and approximately 10 mg, approximately 5 mg and approximately 9 mg, approximately 5 mg and approximately 8 mg, approximately 5 mg and approximately 7 mg, approximately 5 mg and approximately 6 mg, approximately 6 mg and approximately 12 mg, approximately 6 mg and approximately 11 mg, approximately 6 mg and approximately 10 mg, approximately 6 mg and approximately 9 mg, approximately 6 mg and approximately 8 mg, approximately 6 mg and approximately 7 mg, approximately 7 mg and approximately 12 mg, approximately 7 mg and approximately 10 mg, approximately 7 mg and approximately 8 mg, approximately 8 mg and approximately 12 mg, approximately 8 mg and approximately 10 mg, approximately 10 mg and approximately 12 mg, such as greater than or equal to approximately 1 mg, approximately 2 mg, approximately 3 mg, approximately 4 mg, approximately 5 mg, approximately 6 mg, approximately 7 mg, approximately 8 mg, approximately 9 mg, approximately 10 mg, approximately 11 mg, or approximately 12 mg, or less than or equal to approximately 1 mg, approximately 2 mg, approximately 3 mg, approximately 4 mg, approximately 5 mg, approximately 6 mg, approximately 7 mg, approximately 8 mg, approximately 9 mg, approximately 10 mg, approximately 11 mg, or approximately 12 mg of the diclofenac sodium present in one gram of the compounded topical composition. In some embodiments, the amount of diclofenac sodium per gram of the compounded topical composition provided by diclofenac sodium 1.5% solution is approximately 1 mg, approximately 2 mg, approximately 3 mg, approximately 4 mg, approximately 5 mg, approximately 6 mg, approximately 7 mg, approximately 8 mg, approximately 9 mg, approximately 10 mg, approximately 11 mg, or approximately 12 mg.

As introduced above and elsewhere herein, the compounded topical composition may include a diclofenac solution, such as diclofenac sodium topical solution, 1.5% (w/w), compounded with lidocaine and prilocaine cream, 2.5%/2.5%. In various embodiments, the compounded topical composition may comprise lidocaine and prilocaine cream, 2.5%/2.5%, in an amount between approximately 0.2 g and approximately 0.7 g per gram. For example, the topical composition may comprise between approximately 0.2 g and approximately 0.7 g, approximately 0.2 g and approximately 0.6 g, approximately 0.2 g and approximately 0.5 g, approximately 0.2 g and approximately 0.4 g, approximately 0.2 and approximately 0.3 g, approximately 0.3 g and approximately 0.7 g, approximately 0.3 g and approximately 0.6 g, approximately 0.3 g and approximately 0.5 g, approximately 0.3 g and approximately 0.4 g, approximately 0.4 g and approximately 0.7 g, approximately 0.4 g and approximately 0.6 g, approximately 0.4 g and approximately 0.5 g, approximately 0.5 g and approximately 0.6 g, approximately 0.5 g and approximately 0.7 g, approximately 0.6 g and approximately 0.7 g or greater than or equal to approximately 0.1 g, approximately 0.2 g, approximately 0.3 g, approximately 0.4 g, approximately 0.5 g, approximately 0.6 g, or approximately 7 g or less than or equal to approximately 0.7 g, approximately 0.6 g, approximately 0.5 g, approximately 0.4 g, approximately 0.3 g, approximately 0.2 g, or approximately 0.1 g lidocaine and prilocaine cream, 2.5%/2.5%, per gram of compounded topical composition. In one example, the topical composition comprises approximately 0.1 g, approximately 0.2 g, approximately 0.3 g, approximately 0.4 g, approximately 0.5 g, approximately 0.6 g, or approximately 0.7 g lidocaine and prilocaine cream, 2.5%/2.5%, per gram. In one embodiment, the compounded topical composition comprises between approximately 0.5 and approximately 0.9 g lidocaine and prilocaine cream, 2.5%/2.5%, per gram.

In some methods, commercially available lidocaine and prilocaine cream, 2.5%/2.5%, is compounded in an amount between approximately 0.2 g and approximately 0.7 g per gram or in a lesser amount together with lidocaine and prilocaine from other sources sufficient to provide between approximately 5 mg and approximately 17.5 mg of each of the lidocaine and prilocaine present in one gram of the compounded topical composition. For example, lidocaine and prilocaine cream, 2.5%/2.5%, may be added in an amount sufficient to provide between approximately 5 mg and approximately 16 mg, approximately 5 mg and approximately 15 mg, approximately 5 mg and approximately 14 mg, approximately 5 mg and approximately 12 mg, approximately 5 mg and approximately 11 mg, approximately 5 mg and approximately 10 mg, approximately 5 mg and approximately 9 mg, approximately 5 mg and approximately 8 mg, approximately 5 mg and approximately 6 mg, approximately 6 mg and approximately 16 mg, approximately 6 mg and approximately 15 mg, approximately 6 mg and approximately 14 mg, approximately 6 mg and approximately 12 mg, approximately 6 mg and approximately 11 mg, approximately 6 mg and approximately 10 mg, approximately 6 mg and approximately 9 mg, approximately 6 mg and approximately 8 mg, approximately 6 mg and approximately 7 mg, approximately 7 mg and approximately 15 mg, approximately 7 mg and approximately 12 mg, approximately 7 mg and approximately 11 mg, approximately 7 mg and approximately 10 mg, approximately 7 mg and approximately 9 mg, approximately 7 mg and approximately 8 mg, approximately 8 mg and approximately 17.5 mg, approximately 8 mg and approximately 13 mg, approximately 8 mg and approximately 12 mg, approximately 8 mg and approximately 11 mg, approximately 8 mg and approximately 10 mg, approximately 8 mg and approximately 9 mg, approximately 9 mg and approximately 17.5 mg, approximately 9 mg and approximately 16 mg, approximately 9 mg and approximately 15 mg, approximately 9 mg and approximately 14 mg, approximately 9 mg and approximately 13 mg, approximately 9 mg and approximately 12 mg, approximately 9 mg and approximately 11 mg, approximately 9 mg and approximately 10 mg, approximately 10 mg and approximately 17.5 mg, approximately 10 mg and approximately 15 mg, approximately 10 mg and approximately 14 mg, approximately 10 mg and approximately 13 mg, approximately 10 mg and approximately 12 mg, approximately 12 mg and approximately 17.5 mg, approximately 12 mg and approximately 15 mg, approximately 12 mg and approximately 14 mg, approximately 12 mg and approximately 13 mg, approximately 13 mg and approximately 17.5 mg, approximately 13 mg and approximately 16 mg, approximately 13 mg and approximately 15 mg, approximately 13 mg and approximately 14 mg, such as greater than or equal to approximately 5 mg, approximately 6 mg, approximately 7 mg, approximately 8 mg, approximately 9 mg, approximately 10 mg, approximately 11 mg, approximately 12 mg, approximately 13 mg, approximately 14 mg, approximately 15 mg, approximately 16, approximately 17, or approximately 17.5 mg, or less than or equal to approximately 5 mg, approximately 6 mg, approximately 7 mg, approximately 8 mg, approximately 9 mg, approximately 10 mg, approximately 11 mg, approximately 12 mg, approximately 13 mg, approximately 14 mg, approximately 15 mg, approximately 16, approximately 17, or approximately 17.5 mg of each of the lidocaine and prilocaine present in one gram of the compounded topical composition. In some embodiments, the amounts of each of lidocaine and prilocaine per gram of the compounded topical composition provided by lidocaine and prilocaine cream, 2.5%/2.5%, is approximately 1 mg, approximately 2 mg, approximately 3 mg, approximately 4 mg, approximately 5 mg, approximately 6 mg, approximately 7 mg, approximately 8 mg, approximately 9 mg, approximately 10 mg, approximately 11 mg, approximately 13 mg, approximately 14 mg, approximately 15 mg, approximately 16 mg, approximately 17 mg, or approximately 17.5 mg.

As introduced above and elsewhere herein, the compounded composition may comprise lidocaine hydrochloride topical solution such as commercially available lidocaine hydrochloride topical solution, 4%, compounded with commercially available diclofenac sodium topical solution, 1.5% (w/w), and/or commercially available lidocaine and prilocaine cream, 2.5%/2.5%. The compounded topical composition may also comprise lidocaine hydrochloride topical solution, 4%, in an amount between 0 and approximately 0.5 g per gram. For example, the topical composition may comprise lidocaine hydrochloride topical solution, 4%, or equivalent in an amount between approximately 0.001 g and approximately 0.01 g, approximately 0.005 g and approximately 0.02 g, approximately 0.009 g and approximately 0.02 g, approximately 0.09 g and approximately 0.01 g, approximately 0.01 g and approximately 0.02, approximately 0.01 g and approximately 0.1 g, approximately 0.1 g and approximately 0.4 g, approximately 0.1 g and approximately 0.3 g, approximately 0.1 g and approximately 0.2 g, approximately 0.2 and approximately 0.3 g, approximately 0.3 and approximately 0.5, approximately 0.3 g and approximately 0.4 g, or greater than or equal to approximately 0.001 g, approximately 0.01 g, approximately 0.02 g, approximately 0.05 g, approximately 0.1 g, approximately 0.2 g, approximately 0.3 g, or approximately 0.4 g, or less than or equal to approximately 0.001 g, approximately 0.01 g, approximately 0.02 g, approximately 0.05 g, approximately 0.1 g, approximately 0.2 g, approximately 0.3 g, or approximately 0.4 g lidocaine hydrochloride topical solution, 4%, per gram of compounded topical composition. In one example, the topical composition comprises approximately 0.001 g, approximately 0.01 g, approximately 0.02 g, approximately 0.05 g, approximately 0.1 g, approximately 0.2 g, approximately 0.3 g, or approximately 0.4 g lidocaine hydrochloride topical solution, 4%, per gram.

In some methods, lidocaine hydrochloride topical solution, 4%, is compounded in an amount between 0 g and approximately 0.5 g per gram of the compounded topical composition or in an amount sufficient to provide between approximately 1 mg and approximately 20 mg of the lidocaine present in one gram of the compounded topical composition. For example, lidocaine hydrochloride topical solution, 4%, may be added in an amount sufficient to provide between approximately between approximately 0.01 mg and approximately 0.1 mg, approximately 0.1 mg and approximately 3 mg, approximately 0.1 mg and approximately 2 mg, approximately 0.1 mg and approximately 1 mg, approximately 0.1 mg and approximately 0.8 mg, approximately 0.1 mg and approximately 0.6 mg, approximately 0.2 mg and approximately 0.8 mg, approximately 0.2 mg and approximately 0.6 mg, approximately 0.2 mg and approximately 0.5 mg, approximately 0.2 mg and approximately 0.4 mg, approximately 0.2 mg and approximately 0.3 mg, approximately 0.3 mg and approximately 0.8 g, approximately 0.3 mg and approximately 0.6 mg, approximately 0.3 mg and approximately 0.5 mg, approximately 0.3 mg and approximately 0.4 mg, approximately 0.4 mg and approximately 0.8 mg, approximately 0.4 mg and approximately 0.6 mg, approximately 0.6 mg and approximately 0.8 mg, approximately 0.8 mg and approximately 2 mg, approximately 1 mg and approximately 20 mg, approximately 3 mg approximately 15 mg, approximately 3 mg and approximately 10 mg, approximately 5 mg and approximately 15 mg, approximately 5 mg and approximately 10 mg, approximately 10 mg and approximately 15 mg, approximately 15 mg and approximately 20 mg or greater than or equal to approximately 0.1 mg, approximately 0.2 mg, approximately 0.3 mg, approximately 0.4 mg, approximately 0.5 mg, approximately 0.6 mg, approximately 0.8 mg, or approximately 0.9 mg, approximately 1 mg, approximately 3 mg, approximately 5 mg, approximately 10 mg, approximately 15 mg, approximately 20 mg or less than or equal to approximately 0.1 mg, approximately 0.2 mg, approximately 0.3 mg, approximately 0.4 mg, approximately 0.5 mg, approximately 0.6 mg, approximately 0.8 mg, or approximately 0.9 mg, approximately 1 mg, approximately 3 mg, approximately 5 mg, approximately 10 mg, approximately 15 mg, approximately 20 mg lidocaine per gram of compounded topical composition. In some embodiments, the amount of lidocaine per gram of the compounded topical composition provided by lidocaine hydrochloride topical solution, 4%, is approximately 0.1 mg, approximately 0.2 mg, approximately 0.3 mg, approximately 0.4 mg, approximately 0.5 mg, approximately 0.6 mg, approximately 0.8 mg, or approximately 0.9 mg, approximately 1 mg, approximately 3 mg, approximately 5 mg, approximately 10 mg, approximately 15 mg, approximately 20 mg.

As introduced above and elsewhere herein, in some embodiments, the compounded composition may comprise diclofenac sodium topical solution, 1.5% (w/w), lidocaine and prilocaine cream, 2.5%/2.5%, and lidocaine and/or prilocaine bulk powder. Some embodiments may further include lidocaine hydrochloride topical solution, 4%. The compounded topical composition may include between 0 and approximately 40 mg of lidocaine or pharmaceutically acceptable salt or equivalent thereof from bulk powder. For example, the compounded topical composition may comprise lidocaine hydrochloride USP monohydrate powder in an amount between 0 and 50 mg per gram such as between approximately 1 mg and approximately 10 mg, approximately 5 mg and approximately 15 mg, approximately 10 mg and approximately 20 mg, approximately 15 mg and approximately 25 mg, approximately 20 mg and approximately 30 mg, approximately 25 mg and approximately 35 mg, approximately 30 mg and approximately 40 mg, approximately 35 mg and approximately 45 mg, approximately 40 mg and approximately 50 mg, approximately 5 mg and approximately 25 mg, approximately 5 mg and approximately 30 mg, approximately 5 mg and approximately 45 mg, or greater than or equal to approximately 1 mg, approximately 3 mg, approximately 5 mg, approximately 6 mg, approximately 8 mg, approximately 9 mg, approximately 10 mg, approximately 11 mg, approximately 12 mg, approximately 13 mg, approximately 14 mg, approximately 16 mg, approximately 20 mg, approximately 25 mg, approximately 30 mg, approximately 35 mg, approximately 40 mg, approximately 45 mg, or less than or equal to approximately 3 mg, approximately 5 mg, approximately 10 mg, approximately 15 mg, approximately 20 mg, approximately 25 mg, approximately 30 mg, approximately 35 mg, approximately 40 mg, approximately 45 mg, or approximately 50 mg per gram of compounded topical composition. In an example, the topical composition includes approximately 1 mg, approximately 3 mg, approximately 5 mg, approximately 6 mg, approximately 8 mg, approximately 9 mg, approximately 10 mg, approximately 11 mg, approximately 12 mg, approximately 13 mg, approximately 14 mg, approximately 16 mg, approximately 20 mg, approximately 25 mg, approximately 30 mg, approximately 35 mg, approximately 40 mg, approximately 45 mg, or approximately 50 mg of lidocaine hydrochloride USP monohydrate powder per gram of compounded topical composition. Other bulk powders of lidocaine salts or pharmaceutical equivalents may be used in addition or alternatively to lidocaine hydrochloride USP monohydrate in weights providing like amounts of lidocaine active.

Additionally or alternatively, the compounded topical composition may include between 0 and approximately 40 mg of prilocaine or pharmaceutically acceptable salt or equivalent thereof from bulk powder. For example, the compounded topical composition may comprise prilocaine hydrochloride USP powder in an amount between 0 and 50 mg per gram such as between approximately 1 mg and approximately 10 mg, approximately 5 mg and approximately 15 mg, approximately 10 mg and approximately 20 mg, approximately 15 mg and approximately 25 mg, approximately 20 mg and approximately 30 mg, approximately 25 mg and approximately 35 mg, approximately 30 mg and approximately 40 mg, approximately 35 mg and approximately 45 mg, approximately 40 mg and approximately 50 mg, approximately 5 mg and approximately 25 mg, approximately 5 mg and approximately 30 mg, approximately 5 mg and approximately 45 mg, or greater than or equal to approximately 1 mg, approximately 3 mg, approximately 5 mg, approximately 6 mg, approximately 8 mg, approximately 9 mg, approximately 10 mg, approximately 11 mg, approximately 12 mg, approximately 13 mg, approximately 14 mg, approximately 16 mg, approximately 20 mg, approximately 25 mg, approximately 30 mg, approximately 35 mg, approximately 40 mg, approximately 45 mg, or less than or equal to approximately 3 mg, approximately 5 mg, approximately 10 mg, approximately 15 mg, approximately 20 mg, approximately 25 mg, approximately 30 mg, approximately 35 mg, approximately 40 mg, approximately 45 mg, or approximately 50 mg per gram of compounded topical composition. In an example, the topical composition includes approximately 1 mg, approximately 3 mg, approximately 5 mg, approximately 6 mg, approximately 8 mg, approximately 9 mg, approximately 10 mg, approximately 11 mg, approximately 12 mg, approximately 13 mg, approximately 14 mg, approximately 16 mg, approximately 20 mg, approximately 25 mg, approximately 30 mg, approximately 35 mg, approximately 40 mg, approximately 45 mg, or approximately 50 mg of prilocaine hydrochloride USP powder per gram of compounded topical composition. Other bulk powders of prilocaine salts or pharmaceutical equivalents may be used in addition or alternatively to prilocaine hydrochloride USP in weights providing like amounts of prilocaine active.

Various embodiments of the compounded topical composition may include approximately equivalent amounts of lidocaine and prilocaine by weight of the compounded topical composition. Some embodiments may include unmatched amounts of lidocaine and prilocaine.

In various embodiments, the compounded topical composition comprises one or more additional components such as one or more of stabilizers or preservatives, thickeners, surfactants, emulsifiers, solubilizes, skin penetrant enhancers, emollients, or gelling agents. Stabilizers or preservatives may include, for example, one or more of disodium EDTA or a paraben (e.g., methylparaben, propylparaben). In one embodiment, the compounded composition includes one or both of methylparaben or propylparaben. Thickening or gelling agents may include, for example, one or more of acrylic acid or an acrylate, carbomer, carboxypolymethylene, cellulose, hydroxyethyl cellulose, microcrystalline cellulose, carboxymethylcellulose, polyethylene glycol, stearyl palmitate, cetyl alcohol, waxes, titanium dioxide, or combination thereof. In various embodiments, the compounded topical composition comprises between approximately 5 mg and approximately 70 mg thickening agent by weight, such as between approximately 1 mg and approximately 50 mg. Surfactants or emulsifiers may include, for example, one or more of an acrylic, carbomer, polysorbate (e.g., polysorbate 85, polysorbate 20), sorbitan stearate, glyceryl stearate, stearic acid, or emulsifying wax. Solubilizers may include, for example, alcohols or dimethyl isosorbide. Skin penetrant enhancers may include, for example, one or more of DMSO or isopropyl myristate. In some embodiments, the compounded topical composition may comprise xylitol, poloxamers, or both. In one example, the compounded topical composition may include a blend of micronized xylitol and poloxamers sold under the mark LoxaSperse™. In one such example, LoxaSperse™ is present in an amount between approximately 2.5 mg and approximately 20 mg. Some embodiments may include other additional components or composition thereof in addition to or instead of those identified above and elsewhere herein.

In various embodiments, the compounded topical composition comprises an NSAID agent and a local anesthetic agent. The representative amount of NSAID and local anesthetic active agents and actives thereof, e.g., diclofenac, lidocaine, and prilocaine, in the compounded topical composition may be as described above and elsewhere herein.

Various examples of a compounded topical composition comprising between approximately 0.1% and approximately 4% diclofenac sodium, between approximately 0.1% and approximately 4% lidocaine, and between approximately 0.1% and approximately 4% prilocaine by weight are described below and elsewhere herein. In such examples, the compounded topical composition may be compounded by combining diclofenac sodium topical solution, 1.5% (w/w), and lidocaine and prilocaine 2.5%/2.5%. Further examples may also include combining lidocaine hydrochloride topical solution, 4%. Further examples may additionally or alternatively include diclofenac sodium USP powder, lidocaine hydrochloride USP monohydrate powder, prilocaine hydrochloride USP powder, or combination thereof.

In one example, the compounded topical composition comprises a topical pain cream having between approximately 0.5% and approximately 2% diclofenac sodium, between approximately 1% and approximately 3% lidocaine, and between approximately 1% and approximately 3% prilocaine by weight.

In another example, the compounded topical composition comprises a topical pain cream having between approximately 0.75% and approximately 2% diclofenac sodium, between approximately 1.5% and approximately 3% lidocaine, and between approximately 1.5% and approximately 3% prilocaine by weight.

In another example, the compounded topical composition comprises a topical pain cream having between approximately 1% and approximately 2% diclofenac sodium, between approximately 2% and approximately 3% lidocaine, and between approximately 2% and approximately 3% prilocaine by weight.

In another example, the compounded topical composition comprises a topical pain cream having between approximately 1.25% and approximately 2% diclofenac sodium, between approximately 1.5% and approximately 3% lidocaine, and between approximately 1.5% and approximately 3% prilocaine by weight.

In another example, the compounded topical composition comprises a topical pain cream having between approximately 1% and approximately 1.75% diclofenac sodium, between approximately 1.75% and approximately 3% lidocaine, and between approximately 1.75% and approximately 3% prilocaine by weight.

In another example, the compounded topical composition comprises a topical pain cream having between approximately 1.25% and approximately 1.75% diclofenac sodium, between approximately 1.75% and approximately 3% lidocaine, and between approximately 1.75% and approximately 3% prilocaine by weight.

In another example, the compounded topical composition comprises a topical pain cream having between approximately 1.25% and approximately 1.75% diclofenac sodium, between approximately 2% and approximately 3% lidocaine, and between approximately 2% and approximately 3% prilocaine by weight.

In another example, the compounded topical composition comprises a topical pain cream having between approximately 1.5% and approximately 2% diclofenac sodium, between approximately 2.25% and approximately 3% lidocaine, and between approximately 2.25% and approximately 3% prilocaine by weight.

In another example, the compounded topical composition comprises a topical pain cream having between approximately 1.5% and approximately 2% diclofenac sodium, between approximately 2.5% and approximately 3% lidocaine, and between approximately 2.5% and approximately 3% prilocaine by weight.

In another example, the compounded topical composition comprises a topical pain cream having greater than or equal to each of approximately 1.5% diclofenac sodium, approximately 2.5% lidocaine, and approximately 2.5% prilocaine by weight.

In another example, the compounded topical composition comprises a topical pain cream having greater than or equal to each of approximately 1.5% diclofenac sodium, approximately 2.5% lidocaine, and approximately 1.5% prilocaine by weight.

In another example, the compounded topical composition comprises a topical pain cream having greater than approximately 4% diclofenac sodium, less than approximately 4% lidocaine, and less than approximately 4% prilocaine by weight.

Some embodiments of the above examples may include approximately equivalent amounts of lidocaine and prilocaine by weight of the compounded topical composition.

In the above examples, or in other examples or embodiments described herein, compounding the compounded topical composition may comprise combining at least diclofenac sodium topical solution, 1.5% (w/w), lidocaine and prilocaine cream, 2.5%/2.5%, as well as combining one or more of diclofenac sodium UPS bulk powder, lidocaine hydrochloride topical solution, 4%, lidocaine hydrochloride USP monohydrate powder, or prilocaine hydrochloride USP powder in amounts described in the following paragraphs and elsewhere herein.

Diclofenac sodium topical solution, 1.5% (w/w), may be combined in an amount between approximately 10% and approximately 75% diclofenac sodium topical solution, 1.5% (w/w), by weight of the compounded topical composition, for example between approximately 10% and approximately 65%, approximately 20% and approximately 50%, approximately 20% and approximately 60%, approximately 30% and approximately 60%, approximately 30% and approximately 55%, approximately 30% and approximately 50%, or approximately 35% and approximately 45%, or a non-zero percent less than or equal to approximately 70%, approximately 60%, approximately 50%, approximately 45%, approximately 40%, approximately 35%, approximately 25%, approximately 15% by weight of the compounded topical composition. In some embodiments, diclofenac sodium topical solution, 1.5% (w/w), may be compounded in an amount approximately 15%, approximately 20%, approximately 25%, approximately 30%, approximately 35%, approximately 40%, approximately 45%, approximately 50%, approximately 55%, approximately 60%, approximately 65%, or approximately 70% by weight of the compounded topical composition.

Lidocaine and prilocaine cream, 2.5%/2.5%, may be combined in an amount between approximately 10% and approximately 90% lidocaine and prilocaine cream, 2.5%/2.5%, by weight of the compounded topical composition, for example between approximately 20% and approximately 85%, approximately 20% and approximately 65%, approximately 25% and approximately 60%, approximately 30% and approximately 60%, approximately 35% and approximately 60%, approximately 40% and approximately 50%, approximately 45% and approximately 60%, or approximately 45% and approximately 55%, approximately 50% and approximately 90%, approximately 50% and approximately 80%, approximately 50% and approximately 70%, approximately 60% and approximately 90%, approximately 60% and approximately 80%, approximately 70% and approximately 90%, or a non-zero percent less than or equal to approximately 90%, approximately 80%, approximately 70, approximately 60%, approximately 50%, approximately 45%, approximately 40%, approximately 35%, approximately 25%, or approximately 15% by weight of the compounded topical composition. In some embodiments, lidocaine and prilocaine cream, 2.5%/2.5%, may be compounded in an amount approximately 15%, approximately 20%, approximately 25%, approximately 30%, approximately 35%, approximately 40%, approximately 45%, approximately 50%, approximately 53%, approximately 55%, approximately 60%, approximately 65%, or approximately 70% by weight of the compounded topical composition. Some embodiments may include at least 50% lidocaine and prilocaine cream, 2.5%/2.5%, which in some embodiments may include greater than 75% lidocaine and prilocaine cream, 2.5%/2.5%, by weight.

Diclofenac sodium topical solution, 1.5% (w/w), and lidocaine and prilocaine cream, 2.5%/2.5%, may be combined in a combined amount greater than approximately 50%, approximately 60%, approximately 75%, approximately 80%, approximately 85%, approximately 90%, or approximately 95% by weight of the compounded topical composition. Examples may include diclofenac sodium topical solution, 1.5% (w/w), and lidocaine and prilocaine cream, 2.5%/2.5%, combined together in an amount between approximately 50% and approximately 95%, approximately 60% and approximately 95%, approximately 75% and approximately 95%, approximately 80% and approximately 95%, approximately 85% and approximately 90%, approximately 90% and approximately 95% or less than approximately 96%, approximately 95%, approximately 93%, approximately 91%, approximately 85%, approximately 80%, approximately 75%, approximately 70%, or approximately 60% by weight of the compounded topical composition. Further examples, may include diclofenac sodium topical solution, 1.5% (w/w), and lidocaine and prilocaine cream, 2.5%/2.5%, combined together in an amount approximately 95%, approximately 94%, approximately 93%, approximately 92%, approximately 91%, approximately 90%, approximately 85%, approximately 80%, approximately 75%, approximately 70%, or approximately 60% by weight of the compounded topical composition.

Lidocaine and prilocaine cream, 2.5%/2.5%, and diclofenac sodium topical solution, 1.5% (w/w), may be combined at a weight ratio of between approximately 5:1 and approximately 1:5, for example between approximately 4:1 and approximately 1:4, approximately 3:1 and approximately 1:3, approximately 2:1 and approximately 1:2, approximately 1.5:1 and approximately 1:1, approximately 1.3:1 and approximately 1:1, approximately 1:1 and approximately 1:1.5, approximately 1:1.3, or approximately 1:1 and approximately 1:1.5. In some embodiments, lidocaine and prilocaine cream, 2.5%/2.5%, and diclofenac sodium topical solution, 1.5% (w/w), may be combined at a weight ratio of approximately 5:1, approximately 4:1, approximately 3:1, approximately 2:1, approximately 1.5:1, approximately 1.3:1, approximately 1:1, approximately 1:1.3, approximately 1:1.5, approximately 1:2, approximately 1:3, approximately 1:4, or approximately 1:5.

Lidocaine hydrochloride topical solution, 4%, may be combined in an amount between 0 and approximately 20%, or between approximately 1% and approximately 7%, by weight of the compounded topical composition, for example between approximately 1% and approximately 17%, approximately 1% and approximately 15%, approximately 1% and approximately 12%, approximately 1% and approximately 10%, approximately 1% and approximately 7%, approximately 1% and approximately 5%, approximately 1% and approximately 3%, approximately 2% and approximately 7%, or a non-zero percent less than or equal to approximately 20%, approximately 18%, approximately 15%, approximately 13%, approximately 10%, approximately 7%, approximately 5%, or approximately 3% by weight of the compounded topical composition. In some embodiments, lidocaine hydrochloride topical solution, 4%, may be compounded in an amount approximately 20%, approximately 18%, approximately 15%, approximately 13%, approximately 10%, approximately 7%, approximately 5%, approximately 3%, approximately 2%, or approximately 0.9% by weight of the compounded topical composition.

Lidocaine and prilocaine cream, 2.5%/2.5%, and lidocaine hydrochloride topical solution, 4%, may be combined in some examples at a weight ratio of between approximately 800:1 and approximately 1:4, for example between approximately 800:1 and approximately 1:2, approximately 400:1 and approximately 1:1, approximately 400:1 and approximately 10:1, approximately 200:1 and approximately 10:1, approximately 100:1 and approximately 10:1, approximately 75:1 and approximately 10:1, approximately 60:1 and approximately 25:1, approximately 55:1 and approximately 35:1, approximately 55:1 and approximately 40:1, approximately 55:1 and approximately 45:1, or approximately 53:1 and approximately 50:1. In some embodiments, lidocaine and prilocaine cream, 2.5%/2.5%, and lidocaine hydrochloride topical solution, 4%, may be combined at a weight ratio of approximately 800:1, approximately 400:1, approximately 200:1, approximately 100:1, approximately 75:1, approximately 65:1, approximately 60:1, approximately 55:1, approximately 53:1, approximately 52:1, approximately 50:1, approximately 45:1, approximately 40:1, approximately 30:1, approximately 20:1, approximately 4:1, approximately 2:1, approximately 1:1, approximately 1:2, or approximately 1:4.

Diclofenac sodium USP powder may be combined in an amount between 0 and approximately 10%, or between approximately 0.5% and approximately 5%, by weight of the compounded topical composition, for example between approximately 0.1% and approximately 5%, approximately 1% and approximately 5%, approximately 1% and approximately 3%, approximately 1% and approximately 2%, approximately 2% and approximately 5%, approximately 2% and approximately 3%, approximately 0.5% and approximately 1.5%, or approximately 0.5% and approximately 1%, or a non-zero percent less than or equal to approximately 5%, approximately 4.5%, approximately 3.5%, approximately 2.5%, approximately 2%, approximately 1.5%, approximately 1.4%, approximately 1.1%, approximately 1.0%, approximately 0.8%, approximately 0.6%, approximately 0.5%, or approximately 0.1% by weight of the compounded topical composition. In some embodiments, diclofenac sodium USP powder may be compounded in an amount approximately 5%, approximately 4.5%, approximately 3.5%, approximately 2.5%, approximately 2%, approximately 1.5%, approximately 1.4%, approximately 1.1%, approximately 1.0%, approximately 0.8%, approximately 0.6%, approximately 0.5%, or approximately 0.1% by weight of the compounded topical composition.

Diclofenac sodium topical solution, 1.5% (w/w), and diclofenac sodium USP powder may be combined at a weight ratio of between approximately 800:1 and approximately 1:4, for example between approximately 400:1 and approximately 1:2, approximately 200:1 and approximately 1:1, approximately 100:1 and approximately 1:1, approximately 75:1 and approximately 10:1, approximately 60:1 and approximately 25:1, approximately 50:1 and approximately 35:1, approximately 45:1 and approximately 35:1, or approximately 42:1 and approximately 38:1. In some embodiments, diclofenac sodium topical solution, 1.5% (w/w), and diclofenac sodium USP powder may be combined at a weight ratio of approximately 800:1, approximately 400:1, approximately 200:1, approximately 100:1, approximately 75:1, approximately 60:1, approximately 50:1, approximately 45:1, approximately 42:1, approximately 40:1, approximately 38:1, approximately 35:1, approximately 25:1, approximately 10:1, approximately 1:1, or approximately 4:1.

Lidocaine hydrochloride USP monohydrate powder may be combined in an amount between 0 and approximately 6%, or between approximately 0.75% and approximately 5%, by weight of the compounded topical composition, for example between approximately 0.5% and approximately 5%, approximately 0.5% and approximately 4.5%, approximately 0.5% and approximately 3.5%, approximately 0.5% and approximately 2.5%, approximately 0.5% and approximately 1.5%, approximately 1.5% and approximately 5%, approximately 1.5% and approximately 3.5%, approximately 2% and approximately 5%, approximately 3.5% and approximately 5%, or a non-zero percent less than or equal to approximately 6%, approximately 5%, approximately 4%, approximately 3.5%, approximately 3%, approximately 2.5%, approximately 2%, approximately 1.75%, approximately 1.5%, approximately 1.25%, approximately 1%, or approximately 0.5% by weight of the compounded topical composition. In some embodiments, lidocaine hydrochloride USP monohydrate powder may be compounded in an amount approximately 6%, approximately 5%, approximately 4%, approximately 3.5%, approximately 3%, approximately 2.5%, approximately 2%, approximately 1.75%, approximately 1.5%, approximately 1.25%, approximately 1%, or approximately 0.5% by weight of the compounded topical composition.

Lidocaine and prilocaine cream, 2.5%/2.5%, and lidocaine hydrochloride USP monohydrate powder may be combined in some examples at a weight ratio of between approximately 800:1 and approximately 1:4, for example between approximately 800:1 and approximately 1:2, approximately 400:1 and approximately 1:1, approximately 400:1 and approximately 10:1, approximately 200:1 and approximately 10:1, approximately 100:1 and approximately 10:1, approximately 75:1 and approximately 10:1, approximately 60:1 and approximately 25:1, approximately 55:1 and approximately 30:1, approximately 50:1 and approximately 30:1, approximately 45:1 and approximately 35:1, or approximately 40:1 and approximately 35:1. In some embodiments, lidocaine and prilocaine cream, 2.5%/2.5%, and lidocaine hydrochloride USP monohydrate powder may be combined at a weight ratio of approximately 800:1, approximately 400:1, approximately 200:1, approximately 100:1, approximately 75:1, approximately 65:1, approximately 60:1, approximately 55:1, approximately 50:1, approximately 45:1, approximately 40:1, approximately 38:1, approximately 35:1, approximately 30:1, approximately 20:1, approximately 4:1, approximately 2:1, approximately 1:1, approximately 1:2, or approximately 1:4.

Prilocaine hydrochloride USP powder may be combined in an amount between 0 and approximately 6%, or between approximately 0.75% and approximately 5%, by weight of the compounded topical composition, for example between approximately 0.5% and approximately 5%, approximately 0.5% and approximately 4.5%, approximately 0.5% and approximately 3.5%, approximately 0.5% and approximately 2.5%, approximately 0.5% and approximately 1.5%, approximately 1.5% and approximately 5%, approximately 1.5% and approximately 3.5%, approximately 2% and approximately 5%, approximately 3.5% and approximately 5%, or a non-zero percent less than or equal to approximately 6%, approximately 5%, approximately 4%, approximately 3.5%, approximately 3%, approximately 2.5%, approximately 2%, approximately 1.75%, approximately 1.5%, approximately 1.25%, approximately 1%, or approximately 0.5% by weight of the compounded topical composition. In some embodiments, prilocaine hydrochloride USP powder may be compounded in an amount approximately 6%, approximately 5%, approximately 4%, approximately 3.5%, approximately 3%, approximately 2.5%, approximately 2%, approximately 1.75%, approximately 1.5%, approximately 1.25%, approximately 1%, or approximately 0.5% by weight of the compounded topical composition.

Lidocaine and prilocaine cream, 2.5%/2.5%, and prilocaine hydrochloride USP powder may be combined in some examples at a weight ratio of between approximately 800:1 and approximately 1:4, for example between approximately 800:1 and approximately 1:2, approximately 400:1 and approximately 1:1, approximately 400:1 and approximately 10:1, approximately 200:1 and approximately 10:1, approximately 100:1 and approximately 10:1, approximately 75:1 and approximately 10:1, approximately 60:1 and approximately 25:1, approximately 55:1 and approximately 30:1, approximately 50:1 and approximately 30:1, approximately 45:1 and approximately 35:1, or approximately 40:1 and approximately 35:1. In some embodiments, lidocaine and prilocaine cream, 2.5%/2.5%, and prilocaine hydrochloride USP powder may be combined at a weight ratio of approximately 800:1, approximately 400:1, approximately 200:1, approximately 100:1, approximately 75:1, approximately 65:1, approximately 60:1, approximately 55:1, approximately 50:1, approximately 45:1, approximately 40:1, approximately 38:1, approximately 35:1, approximately 30:1, approximately 20:1, approximately 4:1, approximately 2:1, approximately 1:1, approximately 1:2, or approximately 1:4.

The example compounded topical compositions may also include one or more additional components such as one or more of stabilizers or preservatives, thickeners, surfactants, emulsifiers, solubilizes, skin or penetrant enhancers, emollients, or gelling agents. Stabilizers or preservatives may include, for example, one or more of disodium EDTA or a paraben (e.g., methylparaben, propylparaben). In one embodiment, the compounded composition includes one or both of methylparaben or propylparaben. Thickening, which may include gelling, agents may be added to increase viscosity, consistency, or thicken the composition to formulate a lotion, cream, or gel and may include, for example, one or more of acrylic acid or an acrylate, carbomer, carboxypolymethylene, hydroxyethyl cellulose, microcrystalline cellulose, carboxymethylcellulose, polyethylene glycol, waxes, or titanium dioxide. In various embodiments, the compounded topical composition comprises between approximately 0.5% and approximately 7% thickening agent by weight, such as between approximately 1% and approximately 5%. Surfactants or emulsifiers may also be added to emulsify or improve consistency and may include, for example, one or more of an acrylic, carbomer, polysorbate (e.g., polysorbate 85, polysorbate 20), or emulsifying wax. Solubilizers may include, for example, alcohols or dimethyl isosorbide. Skin or penetrant enhancers may include, for example, one or more of DMSO or isopropyl myristate. In some embodiments, the compounded topical composition may comprise xylitol, poloxamers, or both. In one example, the compounded topical composition may include a blend of micronized xylitol and poloxamers sold under the mark LoxaSperse™. In one such example, LoxaSperse™ is present in an amount between approximately 0.25% and approximately 2% by weight. Some embodiments may include other additional components or composition thereof in addition to or instead of those identified above and elsewhere herein.

In some embodiments, the example compounded topical composition comprises between 0.5% and 20% by weight of one or more additional actives, such as anticonvulsants, nerve depressants, muscle relaxants, NMDA (N-Methyl-D-aspartate) receptor antagonists, opiate or opioid agonists, antidepressants, and/or other active agents.

In one embodiment, the compounded topical composition may comprise approximately 1.5% diclofenac sodium, approximately 2.5% lidocaine, and approximately 2.5% prilocaine by weight.

In one such example, the compounded topical composition comprises a topical pain cream having approximately 0.4 g diclofenac sodium 1.5% solution, approximately 0.009 g diclofenac sodium USP powder, approximately 0.528 g lidocaine and prilocaine cream, 2.5%/2.5%, approximately 0.014 g lidocaine hydrochloride USP monohydrate, approximately 0.01 g lidocaine hydrochloride 4% solution, and approximately 0.0138 g prilocaine hydrochloride USP per gram of the compounded topical composition. Each gram of the compounded topical composition may include approximately 15 mg diclofenac sodium and approximately 25 mg of each of lidocaine and prilocaine. The compounded topical composition comprises approximately 40% by weight diclofenac sodium 1.5% solution providing approximately 6 mg diclofenac sodium, approximately 0.9% by weight diclofenac sodium USP powder providing approximately 9 mg diclofenac sodium, approximately 52.8% by weight lidocaine and prilocaine cream, 2.5%/2.5%, providing approximately 13.2 mg of each of lidocaine and prilocaine, approximately 1.4% by weight lidocaine hydrochloride USP monohydrate providing approximately 11.4 mg of lidocaine, approximately 1% by weight lidocaine hydrochloride, 4%, solution providing approximately 0.4 mg of lidocaine, and approximately 1.38% by weight prilocaine hydrochloride USP providing approximately 13.2 mg of prilocaine. In an another embodiment, the compounded composition does not include lidocaine hydrochloride topical solution, 4%, and includes approximately 0.0145 g or approximately 1.45% by weight lidocaine hydrochloride USP monohydrate providing approximately 11.8 mg lidocaine.

In one embodiment, the compounded topical composition may comprise approximately 1.5% diclofenac sodium, approximately 3% lidocaine, and approximately 3% prilocaine by weight.

In one such example, the compounded topical composition comprises a topical pain cream having approximately 0.3 g diclofenac sodium 1.5% solution, approximately 0.0105 g diclofenac sodium USP powder, approximately 0.65 g lidocaine and prilocaine cream, 2.5%/2.5%, approximately 0.012 g lidocaine hydrochloride USP monohydrate, approximately 0.1 g lidocaine hydrochloride, 4%, solution, and approximately 0.016 g prilocaine hydrochloride USP per gram of the compounded topical composition. Each gram of the compounded topical composition may include approximately 15 mg diclofenac sodium and approximately 30 mg of each of lidocaine and prilocaine. The compounded topical composition comprises approximately 30% by weight diclofenac sodium 1.5% solution providing approximately 4.5 mg diclofenac sodium, approximately 1.05% by weight diclofenac sodium USP powder providing approximately 10.5 mg diclofenac sodium, approximately 65% by weight lidocaine and prilocaine cream, 2.5%/2.5%, providing approximately 16.75 mg of each of lidocaine and prilocaine, approximately 1.2% by weight lidocaine hydrochloride USP monohydrate providing approximately 12 mg of lidocaine, approximately 10% by weight lidocaine hydrochloride, 4%, solution providing approximately 4 mg of lidocaine, and approximately 1.6% by weight prilocaine hydrochloride USP providing approximately 13.75 mg of prilocaine. In an another embodiment, the compounded composition does not include lidocaine hydrochloride topical solution, 4%, and includes approximately 0.017 g or approximately 1.7% by weight lidocaine hydrochloride USP monohydrate providing approximately 13.75 mg lidocaine.

The above example embodiments of the compounded topical composition may also include a thickening agent, a preservative, or both. For example, the thickening agent may comprise between approximately 1% and approximately 5% by weight of the compounded topical composition. For example, between approximately 1% and approximately 5% by weight hydroxyethyl cellulose. In one embodiment, the thickening agent may comprise hydroxyethyl cellulose is an amount approximately 0.02 g per gram of compounded topical composition. The preservative may include paraben. For example, the preservative may comprise methylparaben, propylparaben, or both. In one formulation methylparaben is combined in an amount between approximately 0.1 mg and approximately 1 mg, e.g., approximately 0.25 mg, and propylparaben is combined in an amount between 0.1 mg and approximately 1 mg, e.g., approximately 0.125 mg, per gram of the topical composition. Xylitol, poloxamers, or both may also be included. For example, the compounded topical composition may include between 1 mg and 20 mg of xylitol, poloxamers, or both. In one embodiment, the compounded topical composition contains up to 5% LoxaSperse™, such as approximately 5 mg LoxaSperse™. In at least one embodiment, the compounded topical composition includes greater than 5% LoxaSperse™ by weight.

Combining the ingredients may include mixing the ingredients to generate a smooth consistent cream. In one example, the ingredients may be added to a mixing bowl and then mixed to thoroughly wet powders with the cream and/or solutions. The mixed ingredients may be further milled, for example, with a three-roll mill and then packaged.

Some embodiments may not include a commercially available lidocaine solution such as a lidocaine hydrochloride topical solution, 4%. One such embodiment or another embodiment may not include one or more of a lidocaine, prilocaine, or diclofenac bulk powder. A method of making an above or another embodiment of the compounded topical composition described herein, may not include combining additional thickening agents, preservatives, or both, not already present in the combined commercially available medicated compositions, e.g., diclofenac sodium topical solution, 1.5% (w/w), lidocaine hydrochloride topical solution, 4%, or lidocaine and prilocaine cream, 2.5%/2.5%.

In various embodiments, the compounded topical composition comprises a topical pain cream including lidocaine hydrochloride topical solution, 4%, such as those described above, for example. The lidocaine hydrochloride topical solution, 4% may be present in a non-zero amount to approximately 20% by weight, such as between approximately 0.1% and approximately 20%, approximately 0.1% and approximately 15%, approximately 0.1% and approximately 10%, approximately 0.1% and approximately 7%, approximately 0.1% and approximately 4%, approximately 1% and approximately 20%, approximately 1% and approximately 15%, approximately 1% and approximately 10%, approximately 1% and approximately 7%, approximately 1% and approximately 4%, approximately 2% and approximately 10%, approximately 2% and approximately 5%, approximately 5% and approximately 20%, approximately 5% and approximately 15%, approximately 5% and approximately 10%, approximately 5% and approximately 7%, approximately 7% and approximately 20%, approximately 7% and approximately 15%, approximately 7% and approximately 10%, approximately 10% and approximately 20%, approximately 10% and approximately 15%, or approximately 15% and approximately 20%. In some embodiments greater than 20% lidocaine hydrochloride topical solution, 4% may be used, such as greater than 40%, greater than 60%, or greater than 80%.

In various embodiments, the topical pain cream may also include one or more active drugs selected from an local anesthetics, NSAIDS, analgesics, antidepressants, anticonvulsants, opioids, NMDA receptor antagonists, muscle relaxants, or combination thereof.

For example, the compounded topical composition may include a topical pain cream including lidocaine hydrochloride topical solution, 4% and one or more additional actives comprising an NSAID wherein the NSAID is selected from one or more salicylic acid derivatives (e.g., aspirin, diflunisal, salsalate, trilisate), one or more propionic acids (e.g., flurbiprofen, ibuprofen, ketoprofen, naproxen, oxaprozin), one or more acetic acids (e.g., diclofenac, etodolac, indomethacin, ketorolac, nabumetone, sulindac, tolmetin), one or more fenamates (e.g., meclofenamate), one or more oxicams (meloxicam, piroxicam), or one or more COX-2 inhibitors (e.g., celecoxib, rofecoxib, valdecoxib), or combinations thereof. For example, in one embodiment, the compounded topical composition comprises a topical pain cream including xylitol, poloxamer, and one or more actives comprising an comprising a benzeneacetic acid derivative such as diclofenac. Various embodiments may include between approximately 0.01% and approximately 20% by weight NSAID.

In an above or another example, the compounded topical composition may include a topical pain cream including lidocaine hydrochloride topical solution, 4% and one or more actives comprising a local anesthetic selected from lidocaine, prilocaine, benzocaine, or combination thereof. Various embodiments may include between approximately 0.01% and approximately 10% by weight local anesthetic.

In an above or another example, the compounded topical composition may include a topical pain cream including lidocaine hydrochloride topical solution, 4% and one or more actives comprising an anticonvulsant, which may include nerve depressant, selected from gabapentin, topiramate, lamotrigine, or combinations thereof. In various embodiments, the anticonvulsant or nerve depressant agent may comprise between approximately 0.01% and approximately 20% by weight of the topical pain cream.

In an above or another example, the compounded topical composition may include a topical pain cream including lidocaine hydrochloride topical solution, 4% and one or more actives comprising a NMDA receptor antagonists such as ketamine.

In an above or another example, the compounded topical composition may include a topical pain cream including lidocaine hydrochloride topical solution, 4% and one or more actives comprising an opiate, which may include an opioid agonist, selected from tramadol; one or more C2 opiate agonists selected from oxycodone, morphine, methadone, hydromorphone, and fentanyl; one or more C3 opiate agonists selected from hydrocodone, codeine, propoxyphene, butalbital, and pentazocine; or any combination thereof.

In an above or another example, the compounded topical composition may include a topical pain cream including lidocaine hydrochloride topical solution, 4% and one or more actives comprising a muscle relaxant comprising one or more muscle relaxants selected from baclofen, carisoprodol, chlorzoxazone, cyclobenzaprine, dantrolene, diazepam, metaxalone, methocarbamol, orphenadrine, quinine sulfate, tizanidine, and/or other muscle relaxants. In various embodiments, the muscle relaxant agent comprises between approximately 0.001% and approximately 5% by weight of the topical pain cream.

In an above or another example, the compounded topical composition may include a topical pain cream including lidocaine hydrochloride topical solution, 4% and one or more actives including a NSAID including diclofenac and a local anesthetic including lidocaine and prilocaine. In one embodiment, lidocaine may be provided by a lidocaine solution, lidocaine and prilocaine cream, lidocaine bulk powder, or both. Diclofenac may be provided by a diclofenac solution, diclofenac bulk powder, or both, for example. In a further embodiment, the composition may include xylitol, one or more poloxamers, or both.

In various embodiments, a method of compounding a topical pain cream comprises formulating a cream comprises combining lidocaine hydrochloride topical solution, 4% in a weight percent between approximately 0.1% and approximately 7% or in another weight percent described above or elsewhere herein. The method may also include combining one or more active drugs introduced above selected from an analgesics, local anesthetics, NSAIDS, antidepressants, anticonvulsants, opioids, NMDA receptor antagonists, muscle relaxants, or combination thereof.

In one example, the method includes combining the ingredients with a cream base or another base that when mixed with the ingredients, which may include additional ingredients such as thickeners, water, alcohol, solvents, emulsifiers, emollients, for example, generates a cream. For example, ingredients including water or alcohol may be combined with an anhydrous base. In some embodiments, the base includes a commercially available base, such as a cream base, for compounding. In one embodiment, all or a portion of the base portion, such as a cream base, is provided by a commercially available medicated topical cream, ointment, paste, or solution. In one example, the method includes combining the ingredients with components of a cream base, such as thickeners, surfactants, emulsifiers, water, alcohol, solvents, oils, waxes, hydrocarbons, emollients, or combination thereof. Thickening or gelling agents may include, for example, one or more of acrylic acid or an acrylate, carbomer, carboxypolymethylene, cellulose, hydroxyethyl cellulose, microcrystalline cellulose, carboxymethylcellulose, polyethylene glycol, stearyl palmitate, cetyl alcohol, waxes, titanium dioxide, or combination thereof. Some embodiments may include other thickening or gelling agents may be used in addition to or instead of those identified above and elsewhere herein. Surfactants or emulsifiers may include, for example, one or more of an acrylic, carbomer, polysorbate (e.g., polysorbate 85, polysorbate 20), sorbitan stearate, glyceryl stearate, stearic acid, or emulsifying wax. Some embodiments may include other surfactants or emulsifiers in addition to or instead of those identified above and elsewhere herein. Solvents may include, for example, alcohols or dimethyl isosorbide.

Some embodiments may include addition of one or more of stabilizers or preservatives, solubilizes, skin or penetrant enhancers, emollients, or combination thereof. Some embodiments may include other solvents in addition to or instead of those identified above and elsewhere herein. Stabilizers or preservatives may include, for example, one or more of disodium EDTA or a paraben (e.g., methylparaben, propylparaben). Some embodiments may include other stabilizers in addition to or instead of those identified above and elsewhere herein. Skin penetrant enhancers may include, for example, one or more of DMSO or isopropyl myristate. Some embodiments may include other skin penetrant enhancers in addition to or instead of those identified above and elsewhere herein. Emollients may include, for example, natural oils, mineral oil, castor oil, hydrocarbons, antioxidants, lanolin alcohol, or combination thereof. Some embodiments may include other emollients in addition to or instead of those identified above and elsewhere herein.

In various embodiments, the compounded topical composition comprises a topical pain cream including a combination of xylitol and one or more poloxamers. The combination of xylitol and one or more poloxamers may be present in a non-zero amount to approximately 10% by weight, such as between approximately 0.5% and approximately 10%, approximately 0.5% and approximately 7%, approximately 0.5% and approximately 5%, approximately 0.5% and approximately 2%, approximately 1% and approximately 10%, approximately 0.5% and approximately 7%, approximately 1% and approximately 5%, approximately 1% and approximately 3%, approximately 2% and approximately 7%, approximately 2% and approximately 5%, approximately 3% and approximately 7%, or approximately 3% and approximately 5% by weight of the topical pain cream. In one embodiment, the one or more poloxamers comprise poloxamer 407 and poloxamer 188.

In various embodiments, the compounded topical composition may include a topical pain cream comprising xylitol, one or more poloxamers, and one or more active drugs selected from an local anesthetics, NSAIDS, analgesics, antidepressants, anticonvulsants, opioids, NMDA receptor antagonists, muscle relaxants, or combination thereof.

For example, the compounded topical composition comprises a topical pain cream including xylitol, poloxamer, and one or more actives comprising an NSAID wherein the NSAID is selected from one or more salicylic acid derivatives (e.g., aspirin, diflunisal, salsalate, trilisate), one or more propionic acids (e.g., flurbiprofen, ibuprofen, ketoprofen, naproxen, oxaprozin), one or more acetic acids (e.g., diclofenac, etodolac, indomethacin, ketorolac, nabumetone, sulindac, tolmetin), one or more fenamates (e.g., meclofenamate), one or more oxicams (meloxicam, piroxicam), or one or more COX-2 inhibitors (e.g., celecoxib, rofecoxib, valdecoxib), or combinations thereof. For example, in one embodiment, the compounded topical composition comprises a topical pain cream including xylitol, poloxamer, and one or more actives comprising an comprising a benzeneacetic acid derivative such as diclofenac. Various embodiments may include between approximately 0.01% and approximately 20% by weight NSAID.

In an above or another example, the compounded topical composition comprises a topical pain cream including xylitol, poloxamer, and one or more actives comprising a local anesthetic selected from lidocaine, prilocaine, benzocaine, or combination thereof. Various embodiments may include between approximately 0.01% and approximately 10% by weight local anesthetic.

In an above or another example, the compounded topical composition comprises a topical pain cream including xylitol, poloxamer, and one or more actives comprising an anticonvulsant, which may include nerve depressant, selected from gabapentin, topiramate, lamotrigine, or combinations thereof. In various embodiments, the anticonvulsant or nerve depressant agent may comprise between approximately 0.01% and approximately 20% by weight of the topical pain cream.

In an above or another example, the compounded topical composition comprises a topical pain cream including xylitol, poloxamer, and one or more actives comprising a NMDA receptor antagonists such as ketamine.

In an above or another example, the compounded topical composition comprises a topical pain cream including xylitol, poloxamer, and one or more actives comprising an opiate, which may include an opioid agonist, selected from tramadol; one or more C2 opiate agonists selected from oxycodone, morphine, methadone, hydromorphone, and fentanyl; one or more C3 opiate agonists selected from hydrocodone, codeine, propoxyphene, butalbital, and pentazocine; or any combination thereof.

In an above or another example, the compounded topical composition comprises a topical pain cream including xylitol, poloxamer, and one or more actives comprising a muscle relaxant comprising one or more muscle relaxants selected from baclofen, carisoprodol, chlorzoxazone, cyclobenzaprine, dantrolene, diazepam, metaxalone, methocarbamol, orphenadrine, quinine sulfate, tizanidine, and/or other muscle relaxants. In various embodiments, the muscle relaxant agent comprises between approximately 0.001% and approximately 5% by weight of the topical pain cream.

In an above or another example, the compounded topical composition comprises a topical pain cream including xylitol, poloxamer, and one or more actives including a NSAID including diclofenac and a local anesthetic including lidocaine and prilocaine. In one embodiment, lidocaine may be provided by a lidocaine solution, lidocaine and prilocaine cream, lidocaine bulk powder, or both. Diclofenac may be provided by a diclofenac solution, diclofenac bulk powder, or both, for example.

In various embodiments, a method of compounding a topical pain cream comprises formulating a cream comprising combining xylitol and one or more poloxamers in a weight percent between approximately 0.1% and approximately 5% or in another weight percent described above or elsewhere herein. In one embodiment, the one or more poloxamers comprise poloxamer 407 and poloxamer 188. The method may also include combining one or more active drugs selected from an analgesics, local anesthetics, NSAIDS, antidepressants, anticonvulsants, opioids, NMDA receptor antagonists, muscle relaxants, or combination thereof.

In one example, the method includes combining the ingredients with a cream base or another base that when mixed with the ingredients, which may include additional ingredients such as thickeners, water, alcohol, solvents, emulsifiers, emollients, for example, generates a cream. For example, ingredients including water or alcohol may be combined with an anhydrous base. In some embodiments, the base includes a commercially available base, such as a cream base, for compounding. In one embodiment, all or a portion of the base, such as a cream base, is provided by a commercially available medicated topical cream, ointment, paste, or solution. In one example, the method includes combining the ingredients with components of a cream base, such as thickeners, surfactants, emulsifiers, water, alcohol, solvents, oils, waxes, hydrocarbons, emollients, or combination thereof. Thickening or gelling agents may include, for example, one or more of acrylic acid or an acrylate, carbomer, carboxypolymethylene, cellulose, hydroxyethyl cellulose, microcrystalline cellulose, carboxymethylcellulose, polyethylene glycol, stearyl palmitate, cetyl alcohol, waxes, titanium dioxide, or combination thereof. Some embodiments may include other thickening or gelling agents may be used in addition to or instead of those identified above and elsewhere herein. Surfactants or emulsifiers may include, for example, one or more of an acrylic, carbomer, polysorbate (e.g., polysorbate 85, polysorbate 20), sorbitan stearate, glyceryl stearate, stearic acid, or emulsifying wax. Some embodiments may include other surfactants or emulsifiers in addition to or instead of those identified above and elsewhere herein. Solvents may include, for example, alcohols or dimethyl isosorbide. In one embodiment, the compounded topical composition comprises an anhydrous ointment comprising xylitol, one or more poloxamers, and one or more actives according the embodiments described elsewhere herein with respect to creams.

Some embodiments may include addition of one or more of stabilizers or preservatives, solubilizes, skin or penetrant enhancers, emollients, or combination thereof. Some embodiments may include other solvents in addition to or instead of those identified above and elsewhere herein. Stabilizers or preservatives may include, for example, one or more of disodium EDTA or a paraben (e.g., methylparaben, propylparaben). Some embodiments may include other stabilizers in addition to or instead of those identified above and elsewhere herein. Skin penetrant enhancers may include, for example, one or more of DMSO or isopropyl myristate. Some embodiments may include other skin penetrant enhancers in addition to or instead of those identified above and elsewhere herein. Emollients may include, for example, natural oils, mineral oil, castor oil, hydrocarbons, antioxidants, lanolin alcohol, or combination thereof. Some embodiments may include other emollients in addition to or instead of those identified above and elsewhere herein.

The compounded topical compositions comprising a topical pain cream described herein may comprise a water content of approximately 5% or more. For example, the water content may be between approximately 5% and approximately 80%, approximately 5% and approximately 70%, approximately 5% and approximately 65%, approximately 5% and approximately 50%, approximately 5% and approximately 25%, approximately 5% and approximately 15%, approximately 10% and approximately 80%, approximately 10% and approximately 60%, approximately 10% and approximately 45%, approximately 10% and approximately 25%, approximately 10% and approximately 15%, approximately 20% and approximately 80%, approximately 20% and approximately 60%, approximately 20% and approximately 45%, approximately 20% and approximately 25%, approximately 30% and approximately 80%, approximately 30% and approximately 60%, approximately 30% and approximately 45%, approximately 40% and approximately 80%, approximately 40% and approximately 60%, approximately 40% and approximately 50%, approximately 50% and approximately 80%, approximately 50% and approximately 70%, approximately 50% and approximately 60%, approximately 60% and approximately 80%, approximately 60% and approximately 70%, approximately 70% and approximately 80%, approximately 8% or greater, approximately 10% or greater, approximately 15% or greater, approximately 20% or greater, approximately 25% or greater, approximately 30% or greater, approximately 35% or greater, approximately 45% or greater, approximately 55% or greater, approximately 65% or greater, approximately 75% or greater, approximately 80%. In one embodiment, the water content may be approximately 80% or greater. In another embodiment, the water content may be less than 5%.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular preferred arrangements disclosed for carrying out this invention, but that the invention will include all embodiments and arrangements falling within the scope of the appended claims.

Various elements described herein have been described as alternatives or alternative combinations, e.g., in a lists of selectable actives, ingredients, or compositions. It is to be appreciated that embodiments may include one, more, or all of any such elements. Thus, this description includes embodiments of all such elements independently and embodiments including such elements in all combinations.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a range is stated as 1 to 50, it is intended that values such as 2 to 40, 10 to 30, 1 to 3, or 2, 25, 39 and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" or "about" are intended to include +/−10% of the number modified.

What is claimed is:

1. A method of compounding a topical cream, the method comprising:
   combining ingredients comprising:
      lidocaine and prilocaine, 2.5%/2.5%, cream,
      diclofenac sodium, 1.5%, topical solution, comprising DMSO 45.5% (w/w) and
      propylene glycol,
      lidocaine hydrochloride, 4%, topical solution,
      diclofenac sodium USP powder,
      lidocaine hydrochloride USP monohydrate powder, and
      prilocaine hydrochloride USP powder; and
   mixing the ingredients to generate a cream.

2. The method of claim 1, further comprising combining xylitol, a poloxamer, or both.

3. The method of claim 1, further comprising combining one or more parabens.

4. The method of claim 3, wherein the one or more parabens comprises methylparaben and propylparaben.

5. The method of claim 1, further comprising combining a thickening agent.

6. The method of claim 1, wherein the diclofenac sodium, 1.5%, topical solution, is combined in an amount between approximately 20% and approximately 50% by weight of the compounded topical cream, and wherein the lidocaine and prilocaine, 2.5%/2.5%, cream is combined in an amount at least 50% by weight of the compounded topical cream.

7. The method of claim 6, wherein the lidocaine hydrochloride, 4%, topical solution is combined in an amount between approximately 1% and approximately 7% by weight of the compounded topical cream, wherein the diclofenac sodium USP powder is combined in an amount between approximately 0.5% and approximately 5% by weight of the compounded topical cream, wherein the lidocaine hydrochloride USP monohydrate powder is combined in an amount between 0.75% and approximately 5% by weight of the compounded topical cream, and wherein the prilocaine hydrochloride USP powder is combined in an amount between 0.75% and approximately 5% by weight of the compounded topical cream.

8. The method of claim 7, further comprising combining at least one of methylparaben or propylparaben and at least one of xylitol or poloxamer.

9. The method of claim 8, further comprising combining a thickening agent in an amount between approximately 1% and approximately 5% by weight of the compounded topical cream.

10. The method of claim 9, wherein the ingredients are combined in amounts such that the compounded topical cream comprises approximately 1.5% by weight diclofenac sodium, approximately 2.5% by weight lidocaine, and approximately 2.5% by weight prilocaine.

11. The method of claim 10, wherein the thickening agent comprises hydroxyethyl cellulose.

* * * * *